US010241124B2

(12) United States Patent
Augstein et al.

(10) Patent No.: US 10,241,124 B2
(45) Date of Patent: Mar. 26, 2019

(54) METHOD TO PERFORM A MEASUREMENT OF AN ANALYTE IN A SAMPLE USING AN AUTOMATIC ANALYZER

(71) Applicant: Roche Diagnostics Operations, Inc., Indianapolis, IN (US)

(72) Inventors: Manfred Augstein, Mannheim (DE); Nadine Losleben, Munich (DE); Thorsten Brueckner, Schriesheim (DE); Christoph Boehm, Viernheim (DE); Juergen Spinke, Lorsch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 188 days.

(21) Appl. No.: 15/092,806

(22) Filed: Apr. 7, 2016

(65) Prior Publication Data

US 2016/0216289 A1 Jul. 28, 2016

Related U.S. Application Data

(63) Continuation of application No. PCT/EP2014/071131, filed on Oct. 2, 2014.

(30) Foreign Application Priority Data

Oct. 8, 2013 (EP) .................................... 13187717

(51) Int. Cl.
| | |
|---|---|
| *C12M 1/00* | (2006.01) |
| *G01N 35/10* | (2006.01) |
| *B01L 3/02* | (2006.01) |
| *G01F 11/08* | (2006.01) |
| *B01L 3/00* | (2006.01) |
| *G01N 35/00* | (2006.01) |

(52) U.S. Cl.
CPC .......... *G01N 35/1002* (2013.01); *B01L 3/021* (2013.01); *B01L 3/50273* (2013.01); *B01L 3/502715* (2013.01); *B01L 3/502738* (2013.01); *G01F 11/082* (2013.01); *G01F 11/086* (2013.01); *G01F 11/088* (2013.01); *G01N 35/00871* (2013.01); *B01L 2200/027* (2013.01); *B01L 2200/04* (2013.01); *B01L 2300/02* (2013.01); *B01L 2300/042* (2013.01); *B01L 2300/0609* (2013.01); *B01L 2300/0663* (2013.01); *B01L 2300/123* (2013.01); *B01L 2400/0481* (2013.01); *G01N 2035/1034* (2013.01)

(58) Field of Classification Search
CPC .......... B01L 2200/027; B01L 2200/04; B01L 2300/02; B01L 2300/042; B01L 2300/0609; B01L 2300/0663; B01L 2300/123; B01L 2400/0481; B01L 3/021; B01L 3/502715; B01L 3/50273; B01L 3/502738; G01F 11/082; G01F 11/086; G01F 11/088; G01N 2035/1034; G01N 35/00871; G01N 35/1002
USPC ...................................................... 435/283.1
See application file for complete search history.

(56) References Cited

U.S. PATENT DOCUMENTS

| | | | |
|---|---|---|---|
| 3,836,335 A | 9/1974 | Eppes | |
| 4,158,035 A | 6/1979 | Haase et al. | |
| 4,236,516 A | 12/1980 | Nilson | |
| 5,343,909 A | 9/1994 | Goodman | |
| 5,675,715 A | 10/1997 | Bernstein et al. | |
| 5,947,167 A * | 9/1999 | Bogen .................. | B01L 3/0293 141/1 |
| 6,062,430 A | 5/2000 | Fuchs | |
| 6,193,933 B1 | 2/2001 | Sasaki et al. | |
| 8,752,732 B2 | 6/2014 | Evans et al. | |
| 2001/0048899 A1 * | 12/2001 | Marouiss ............ | B01L 3/50853 422/505 |
| 2003/0223910 A1 | 12/2003 | Jackson, III et al. | |
| 2004/0058452 A1 | 3/2004 | Fisher et al. | |
| 2011/0297677 A1 | 12/2011 | Py et al. | |

FOREIGN PATENT DOCUMENTS

| | | |
|---|---|---|
| EP | 0095401 A1 | 11/1983 |
| EP | 1959257 A2 | 8/2008 |
| JP | 2000-137033 A | 5/2000 |
| JP | 2002-181838 A | 6/2002 |

(Continued)

OTHER PUBLICATIONS

International Search Report dated Dec. 15, 2014, in Application No. PCT/EP2014/071131, 5 pages.

*Primary Examiner* — Cynthia B Wilder
(74) *Attorney, Agent, or Firm* — Roche Diagnostics Operations, Inc.

(57) ABSTRACT

A method of performing a measurement of an analyte in a sample using an automatic analyzer is provided. The automatic analyzer comprises: a cartridge for dispensing a fluid, a measurement unit for performing the measurement, a sample holder for receiving the sample, and a pump for pumping the fluid out of the cartridge and into the sample holder. The cartridge comprises: a rigid portion, a flexible bladder, and an outlet. The rigid portion comprises an opening, which is connected to an inner cavity. The flexible bladder seals the opening to form a fluid chamber from the inner cavity. The fluid chamber is at least partially filled with the fluid. The pump is connected to the outlet. The method comprises: placing the sample into the sample holder, controlling the pumping of the fluid from the cartridge into the sample holder, and performing the measurement of the analyte using the measurement unit.

20 Claims, 21 Drawing Sheets

(56) References Cited

FOREIGN PATENT DOCUMENTS

| WO | 1995/004691 A1 | 2/1995 |
| WO | 2002040122 A2 | 5/2002 |
| WO | WO 0240122 * | 5/2002 |
| WO | 2002092228 A2 | 11/2002 |
| WO | 2006/048678 A2 | 5/2006 |
| WO | 2010/042902 A1 | 4/2010 |

\* cited by examiner

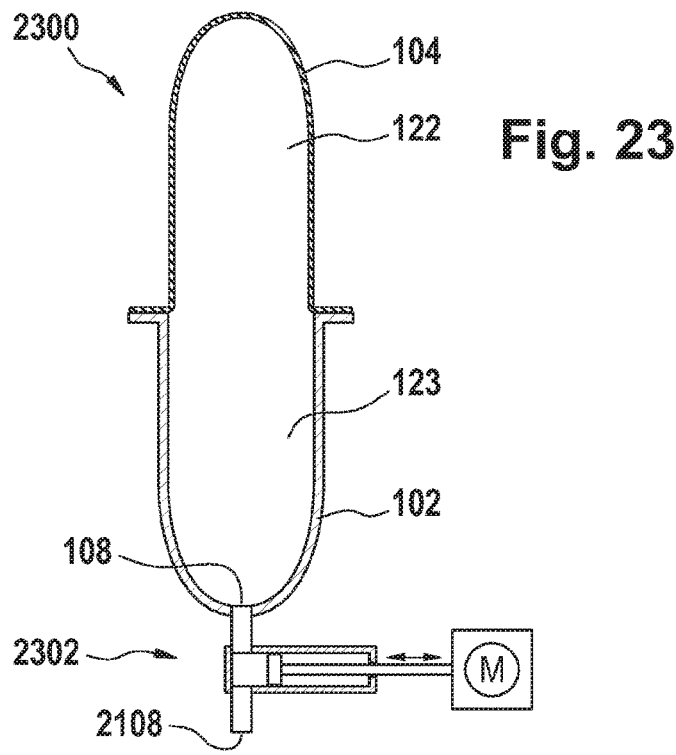
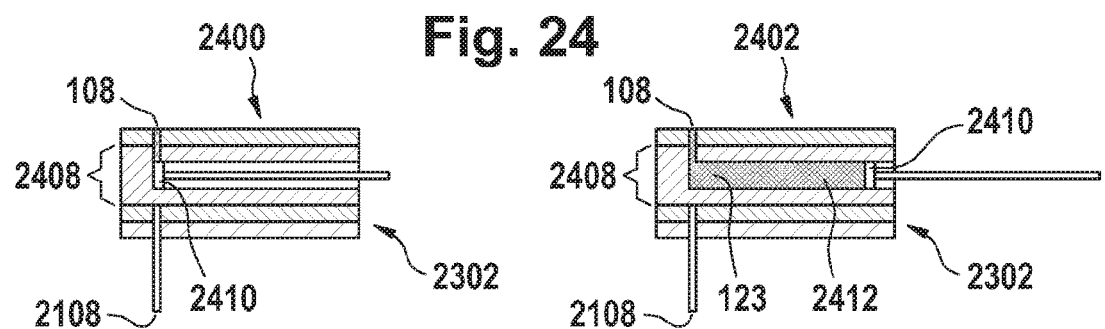
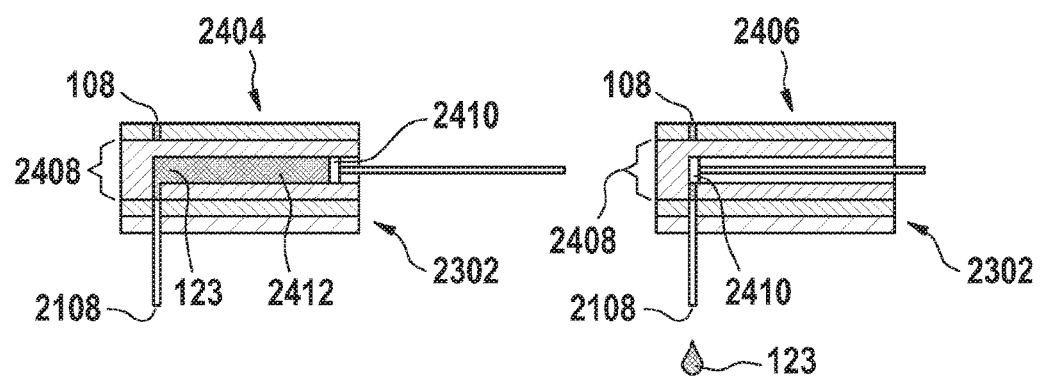

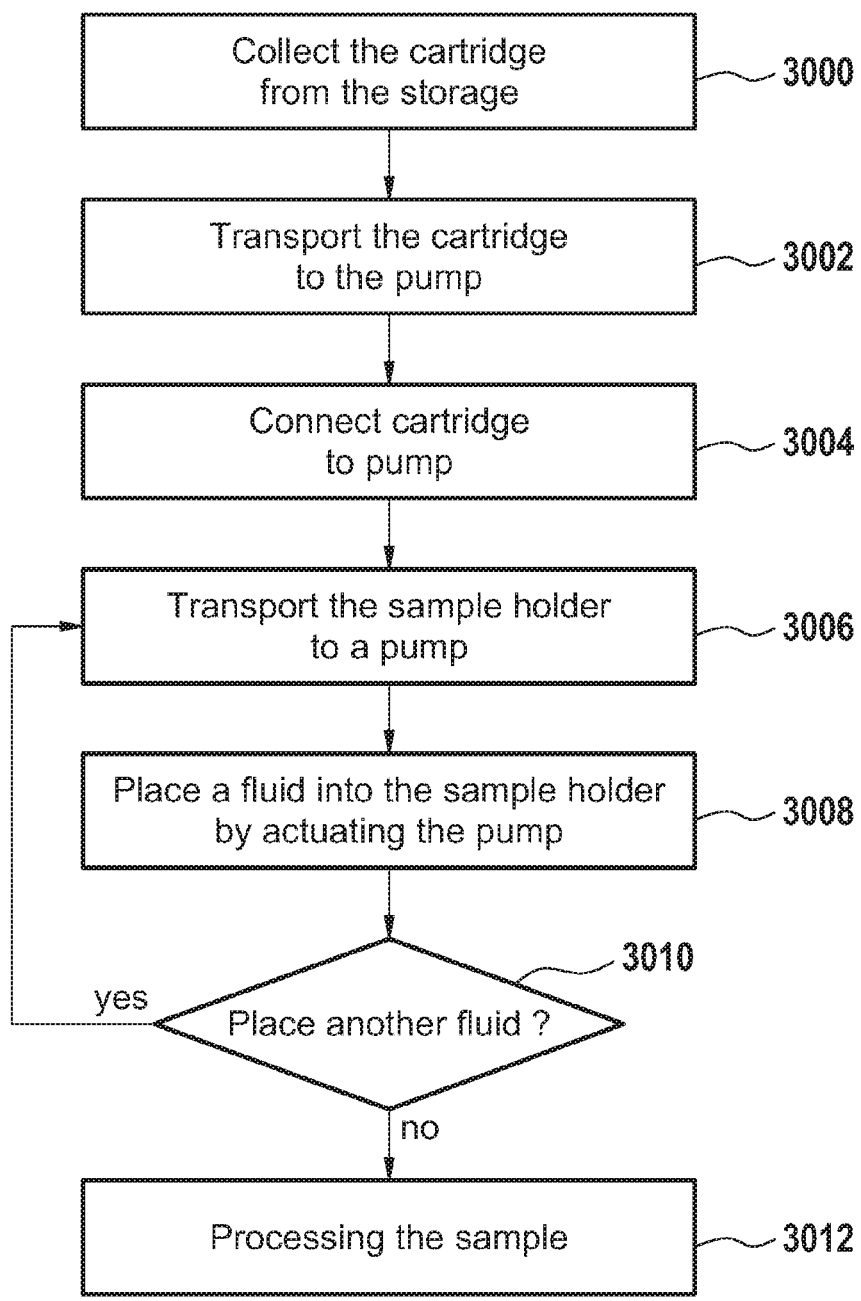

METHOD TO PERFORM A MEASUREMENT OF AN ANALYTE IN A SAMPLE USING AN AUTOMATIC ANALYZER

CROSS-REFERENCE TO RELATED APPLICATIONS

This application is a continuation of International Patent Application No. PCT/EP2014/071131 filed 2 Oct. 2014, which claims the benefit of European Patent Application No. 13187717.7 filed 8 Oct. 2013, the disclosures of which are hereby incorporated by reference in their entirety.

TECHNICAL FIELD

The disclosure relates to the measurement of an analyte in a sample and, in particular, to cartridges for automatic analyzers.

BACKGROUND

In medical laboratories, in vitro diagnostic tests are commonly performed on biological samples. Such tests may be performed manually using pipettes or may be performed using an automatic analyzer. Automatic analyzers may automatically add reagents to the biological sample in order to determine the amount of a substance of interest in a biological sample.

BRIEF SUMMARY

It is against the above background that the embodiments of the present disclosure provide certain unobvious advantages and advancements over the prior art. In particular, the inventors have recognized a need for improvements in methods to perform a measurement of an analyte in a sample using an automatic analyzer, and a cartridge assembly.

In accordance with one embodiment of the present disclosure, a method of performing a measurement of an analyte in a sample using an automatic analyzer is provided, wherein the automatic analyzer comprises: a cartridge for dispensing a fluid, a measurement unit for performing the measurement, a sample holder for receiving the sample, and a pump for pumping the fluid out of the cartridge and into the sample holder. The cartridge comprises: a rigid portion, a flexible bladder, and an outlet, wherein the outlet is attached to the rigid portion; wherein the rigid portion comprises an inner cavity; wherein the outlet is connected to the inner cavity; wherein the rigid portion comprises an opening; wherein the opening is connected to the inner cavity; wherein the flexible bladder seals the opening to form a fluid chamber from the inner cavity; wherein the fluid chamber is at least partially filled with the fluid; and wherein the pump is connected to the outlet. The method comprises: placing the sample into the sample holder; controlling the pumping of the fluid from the cartridge into the sample holder; and performing the measurement of the analyte using the measurement unit.

In accordance with another embodiment of the disclosure, an automatic analyzer for performing a measurement of an analyte in a sample is provided, wherein the automatic analyzer comprises: a cartridge for dispensing a fluid, a measurement unit for performing the measurement, a sample holder for receiving the sample, a pump for pumping the fluid out of the cartridge to the sample holder, a memory for storing machine executable instructions, and a processor for controlling the automatic analyzer. The cartridge comprises: a rigid portion, a flexible bladder, and an outlet, wherein the outlet is attached to the rigid portion; wherein the rigid portion comprises an inner cavity; wherein the outlet is connected to the inner cavity; wherein the rigid portion comprises an opening; wherein the opening is connected to the inner cavity; wherein the flexible bladder seals the opening to form a fluid chamber from the inner cavity; and wherein the fluid chamber is at least partially filled with the fluid. The execution of the instructions causes the processor to: control the pump to pump the fluid from the cartridge to the sample holder; and control the measurement unit to perform the measurement of the analyte.

In accordance with yet another embodiment of the disclosure, a cartridge assembly is provided, wherein the cartridge assembly comprises: a cartridge for dispensing a fluid through an outlet, and a pump for pumping the fluid in the cartridge through the outlet, wherein the cartridge comprises: a rigid portion, and a flexible bladder, wherein the outlet is attached to the rigid portion; wherein the rigid portion comprises an inner cavity; wherein the outlet is connected to the inner cavity; wherein the rigid portion comprises an opening; wherein the opening is connected to the inner cavity; and wherein the flexible bladder seals the opening to form a fluid chamber from the inner cavity.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIGS. 1-5, 7-16 and 19-23 each illustrates an example of a cartridge in accordance with an embodiment of the present disclosure;

FIG. 24 illustrates an example of a pump in accordance with an embodiment of the present disclosure; and FIGS. 26, 28 and 30 each illustrates a method of using an automatic analyzer in accordance with an embodiment of the present disclosure.

Figure 1:
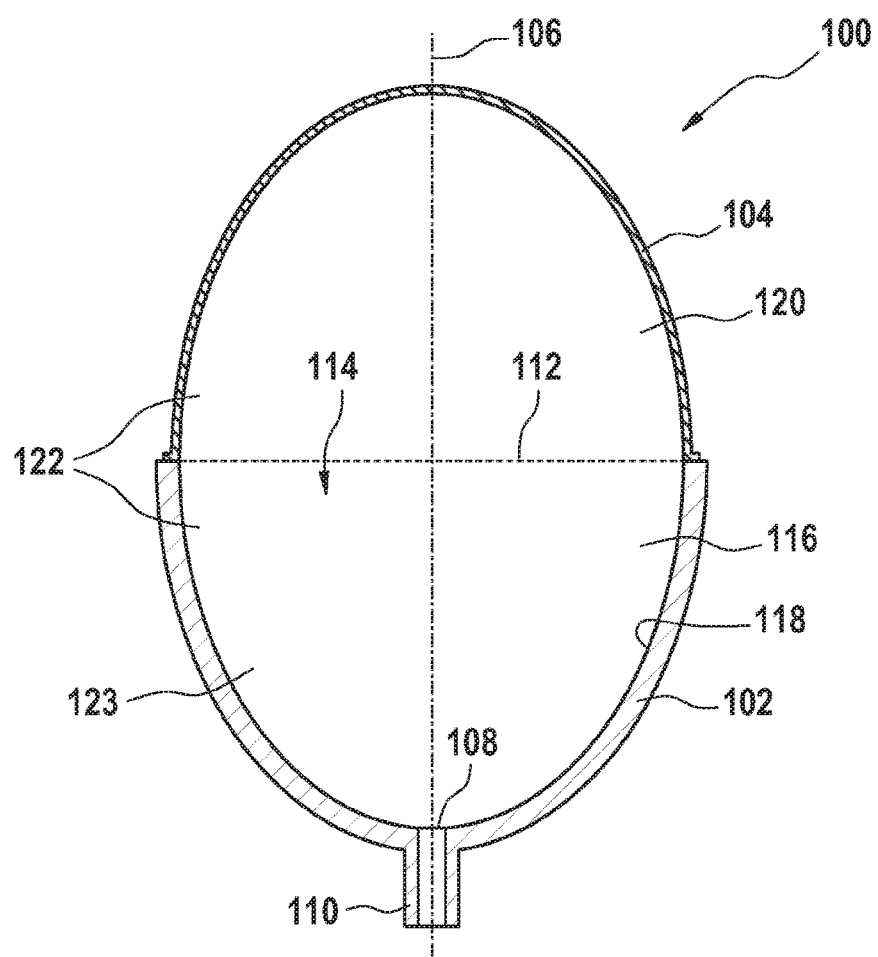

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

Definitions

A 'cartridge' as used herein encompasses a case or container either containing or for containing a fluid that is designed to be inserted into a machine for dispensing the fluid.

A 'controller' as used herein encompasses a device, machine, or apparatus for controlling the operation and/or function of one or more other devices. Examples of a controller may include, but are not limited to: a computer, a processor, an imbedded system or controller, a programmable logic controller, and a microcontroller. A 'computing device' or 'computer' as used herein encompasses any device comprising a processor. A 'processor' as used herein encompasses an electronic component that is able to execute a program or machine executable instruction.

A 'computer-readable storage medium' as used herein encompasses any tangible storage medium that may store instructions, which are executable by a processor of a computing device. The computer-readable storage medium may be referred to as a "computer-readable non-transitory storage medium."

'Computer memory' or 'memory' is an example of a computer-readable storage medium. Computer memory is any memory that is directly accessible to a processor or other controller. 'Computer storage' or 'storage' is an example of a computer-readable storage medium. Computer storage is any non-volatile computer-readable storage medium.

A 'user interface' as used herein is an interface that allows a user or operator to interact with a computer or computer system.

A 'hardware interface' as used herein encompasses an interface that enables a processor or other controller to interact with and/or control an external computing device and/or apparatus. A hardware interface may allow a processor to send control signals or instructions to an external computing device and/or apparatus.

A 'biological sample' as used herein encompasses a sample that comprises material generated by a biological system. A biological system may include parts or products of a living organism or chemicals or materials derived or replicated from an organism. For instance, DNA or RNA may be copied by a PCR process although the material is not directly generated by an organism it was derived originally from a biological system or organism.

In one aspect, the present disclosure provides for a method of performing the measurement of an analyte in the sample using the automatic analyzer. The automatic analyzer comprises a cartridge for dispensing a fluid. A fluid as used herein may encompass a reagent, a diluent, a sample, a biological sample, a stain, a reagent, a calibration standard, a quality control solution, or another biological solution.

The automatic analyzer further comprises a measurement unit for performing the measurement. The measurement unit may for instance perform an optical, electrical, or other physical measurement to measure the analyte.

The automatic analyzer further comprises a sample holder for receiving a sample. The sample holder for instance could be a disc, a microscope slide, a test strip, a cuvette, or other container for holding the sample and/or the fluid.

The automatic analyzer further comprises a pump for pumping the fluid out of the cartridge and into the sample holder.

The cartridge comprises a rigid portion, a flexible bladder, and an outlet. The outlet is attached to the rigid portion. The rigid portion comprises an inner cavity. The outlet is connected to the inner cavity. The rigid portion comprises an opening. The opening is connected to the inner cavity. The flexible bladder seals the opening to form a fluid chamber from the inner cavity. The fluid chamber is at least partially filled with the fluid. The pump is connected to the outlet.

The method comprises the step of placing the sample into the sample holder. The method further comprises the step of controlling the pumping of the fluid from the cartridge into the sample holder. The method further comprises performing the measurement of the analyte using the measurement unit.

The method may have the benefit that the flexible bladder makes the pressure within the inner cavity more uniform and allows more accurate pumping of the fluid out of the cartridge. This for instance may be more accurate than applying a pressure to the flexible bladder to force fluid through the outlet.

In another embodiment the sample is a biological sample.

In another embodiment the sample is a fluid comprising a defined amount of analyte, like a calibration standard or a quality control solution.

In another embodiment the sample is a fluid comprising a defined amount of a substance that is used for performing a measurement of an analyte, like a mass-standard for mass spectroscopy or spectrometry.

In another embodiment the flexible bladder has an exterior surface. The exterior surface is exposed to constant pressure during pumping of the fluid from the cartridge into the sample holder. The constant pressure on the bladder may serve to keep the pressure constant during the pumping process. This may lead to more accurate dispensing of the fluid. The constant pressure could for example be atmosphere pressure. In some examples the exterior surface is exposed to the atmosphere in order to provide the constant pressure.

In another aspect, the present disclosure provides for an automatic analyzer for performing the measurement of an analyte in the sample. The automatic analyzer comprises a cartridge for dispensing a fluid, a measurement unit for performing the measurement, a sample holder for receiving the sample, a pump for pumping the fluid out of the cartridge to the sample holder, a memory for storing the machine-executable instructions and a processor for controlling the automatic analyzer.

The cartridge comprises a rigid portion, a flexible bladder, and an outlet. The outlet is attached to the rigid portion. The rigid portion comprises an inner cavity. The outlet is connected to the inner cavity. The rigid portion comprises an opening. The opening is connected to the inner cavity. The flexible bladder seals the opening to form a fluid chamber from the inner cavity. The fluid chamber is at least partially filled with the fluid.

Execution of the machine-executable instructions causes the processor to control the pump to pump the fluid from the cartridge to the sample holder. Execution of the instructions further causes the processor to control the measurement unit to perform the measurement of the analyte. In some examples execution of the machine-executable instructions also cause the processor to place the sample into the sample holder using for example a sample dispenser. However, in other examples the sample may be placed in the sample holder manually. For instance, a laboratory technician or physician may place the sample into the sample holder and then install it into the automatic analyzer for processing.

In another embodiment the outlet is circular. The outlet has an outlet diameter. The cavity is symmetric about the radius of symmetry. The cavity has a cavity radius about the axis of symmetry. The axis of symmetry passes through the opening and the outlet. The cavity radius is monotonically decreasing from the opening to the outlet.

In another embodiment the cartridge further comprises a valve for sealing and unsealing the outlet and/or wherein the pump comprises the nozzle for dispensing the fluid. There for instance may be a valve in addition to the pump.

In another embodiment the cartridge is detachable from the pump. This may have the advantage that the pump may be reused multiple times.

In another embodiment the pump has an inlet. The automatic analyzer further comprises a sealed coupling for attaching the pump inlet to the cartridge outlet. The sealed coupling for instance may be a connector between the pump inlet and the cartridge outlet. This may facilitate the installation of a cartridge into the pump.

In another embodiment the measurement unit is a test strip analyzer.

In another embodiment the measurement unit is a urine test strip analyzer.

In another embodiment the measurement unit is a fluorescent spectrometer.

In another embodiment the measurement unit is a photospectrometer.

In another embodiment the measurement unit is a spectrometer.

In another embodiment the measurement unit is a scattered light spectrometer.

In another embodiment the measurement unit is a chemiluminescence system.

In another embodiment the measurement unit is an electrochemiluminescence or ECL measurement system.

In another embodiment the measurement unit is a mass spectrometer.

In another embodiment the measurement unit is a cell counter.

In another embodiment the measurement unit is an optical imaging system.

In another embodiment the measurement unit is a staining system.

In another embodiment the measurement unit is a turbidimetric system.

In another embodiment the measurement unit is a nephelometric system.

In another embodiment the cartridge further comprises the fluid.

In another embodiment the automatic analyzer comprises a cartridge assembly. The cartridge assembly comprises the cartridge and the pump.

In another embodiment the pump is permanently attached to the cartridge.

In another embodiment the automatic analyzer further comprises multiple cartridges. The automatic analyzer further comprises a translation mechanism for moving the pump between the multiple cartridges. The translation mechanism is operable for attaching the pump to any one of the multiple cartridges. The translation mechanism is operable for detaching the pump from any one of the multiple cartridges. For example, the translation mechanism may have an apparatus that attaches or detaches a coupling between the multiple cartridges and the pump. The cartridge may be one of the multiple cartridges.

In another embodiment the automatic analyzer further comprises multiple cartridges. The automatic analyzer comprises multiple pumps. The automatic analyzer further comprises a translation mechanism for moving either the sample holder to each of the multiple cartridges or for moving each of the multiple cartridges to the sample holder. The cartridge may be one of the multiple cartridges. The pump may be one of the multiple pumps.

In another aspect, the present disclosure provides for a cartridge assembly. The cartridge assembly comprises a cartridge for dispensing a fluid through an outlet and a pump for pumping the fluid in the cartridge through the outlet. The cartridge comprises a rigid portion and a flexible bladder. The outlet is attached to the rigid portion. The rigid portion comprises an inner cavity. The outlet is connected to the inner cavity. The rigid portion comprises an opening. The opening is connected to the inner cavity. The flexible bladder seals the opening to form a fluid chamber from the inner cavity. This cartridge assembly may have the benefit that the flexible bladder provides a uniform pump that enables more accurate pumping of the fluid in the cartridge through the outlet.

In one example the cartridge comprises a rigid portion. The cartridge further comprises a flexible bladder. The cartridge further comprises an outlet attached to the rigid portion. The rigid portion comprises an inner cavity. The outlet is connected to the inner cavity. The outlet is an outlet where fluid can be expelled from the cartridge. The rigid portion comprises an opening. The opening is connected to the inner cavity. The flexible bladder seals the opening to form a fluid chamber from the inner cavity. This embodiment may be beneficial because the cartridge can dispense fluid without a gas being added to the contents of the fluid chamber. In many cartridges where the cartridge is completely rigid there needs to be a baffle or other inlet to allow gas to equalize the (under-)pressure within the cartridge caused by dispensing of fluid. Use of a flexible bladder enables fluid to be expelled without exposing the fluid remaining in the cartridge to atmosphere gases or other gases.

In one example, when the cartridge is in an operating position the rigid portion is above the outlet.

In one example the rigid portion and/or the flexible bladder are made from: polypropylene, polyethylene, cyclic olefin copolymer (COC), polyamide, and polyimide. The rigid portion and the flexible bladder may be made from different materials. For example the flexible bladder may be aluminized polyethylene and the rigid portion could be made from polypropylene or polyethylene.

In different examples the flexible bladder may be attached to the rigid portion in different ways. For example, the flexible bladder may be attached to the rigid portion using any one of the following: thermo bonding, laser welding, co-extrusion, ultrasonic welding, adhesive bonding, chemical bonding, and press connection with a screw-cap.

In another embodiment, when the fluid chamber is filled with the fluid the flexible bladder is operable to expand out of the inner cavity to form a bladder volume. The bladder volume is defined by the opening and the flexible bladder. The bladder volume as used herein encompasses a volume within the fluid chamber that extends beyond the inner cavity. The flexible bladder is flexible so the bladder volume may change with the amount of material or fluid that is in the fluid chamber. If the flexible bladder is elastic then the bladder volume may also change to represent the expansion or contraction of the flexible bladder.

In another embodiment the flexible bladder is inelastic. When the fluid chamber is fully filled with the fluid the bladder volume is approximately equal to the volume of the inner cavity. By approximately equal it is assumed that the volume of the cavity and the bladder volume are within approximately 10% of each other. The volume of the inner cavity is the space defined by the inner cavity bounded by the outlet and the opening. This embodiment may be beneficial because as the fluid is expelled from the cartridge the flexible bladder will either cover or approximately cover the inner surface of the inner cavity. This may enable the almost complete use of fluid from within the cartridge.

In another embodiment the flexible bladder is elastic. This embodiment may be beneficial because it may enable the fluid to be efficiently expelled from the cartridge. The volume of the bladder volume could be smaller, the same size, or larger than the fluid chamber. This depends upon how elastic the flexible bladder is.

In another embodiment the inner cavity has an inner cavity surface and the flexible bladder is operable to cover the inner cavity surface when the fluid chamber is empty of the fluid. This may be beneficial because if the bladder is covering the cavity surface then fluid has been almost completely expelled from the cartridge. It is stated that the flexible bladder is operable to cover the inner cavity surface when the fluid chamber is empty of the fluid. However, this does not mean that the flexible bladder has to cover the inner cavity surface when there is no fluid in the fluid chamber. For instance, the cartridge could be filled with air or other gas, which would inflate the flexible bladder at least partially. When the flexible bladder is inelastic the flexible bladder may be fitted such that it covers most or all of the inner surface when the cartridge is in an empty condition. That is to say the fluid has been drained or expelled from the cartridge.

When the flexible bladder is elastic the flexible bladder may be fitted such that it stretches to very precisely cover the surface of the inner cavity surface.

In another embodiment the inner cavity has an inner cavity surface. When the fluid chamber is in an empty condition the flexible bladder is operable to cover the inner cavity surface.

In another embodiment the cartridge further comprises a cap. The cap forms a cap cavity. The cap cavity is positioned about the opening. The cap cavity is operable to receive the flexible bladder when filled with the fluid. The cap may serve to provide additional mechanical support for the cartridge and it may also protect the flexible bladder from damage when the flexible bladder extends to form the bladder volume. When the flexible bladder is elastic the cap may also serve to limit the volume of fluid, which can be used to fill the fluid chamber. This may prevent overfilling of the cartridge.

When the cartridge is in an operating position the cap may be above the rigid portion and the cap cavity is positioned about the opening.

In another embodiment the cap is attached to the rigid portion to seal the cap cavity. The cap comprises a gas inlet operable for pressurizing and/or ventilating the cap cavity.

In another embodiment the cartridge comprises a fluid inlet on the rigid portion. The fluid inlet is sealable. This embodiment may be beneficial because it may enable an operator or user of the cartridge to easily fill it with the fluid.

In another embodiment the outlet is circular. The outlet has an outlet diameter. The cavity is symmetric about an axis of symmetry. The cavity has a cavity radius about the axis of symmetry. The axis of symmetry passes through the opening and the outlet. The cavity radius is monotonically decreasing from the opening to the outlet.

In another embodiment the cartridge further comprises a valve for sealing and unsealing the outlet and/or nozzle attached to the outlet for dispensing the fluid and/or a pump for pumping fluid from the fluid chamber.

In another embodiment the cartridge further comprises a pump operable for dispensing the fluid via the outlet.

In another embodiment the cartridge is further operable for dispensing between 0 and 1 picoliters.

In another embodiment the cartridge is further operable for dispensing between 0 and 5 picoliters.

In another embodiment the cartridge is further operable for dispensing between 0 and 10 picoliters.

In another embodiment the cartridge is further operable for dispensing between 0 and 50 picoliters In another embodiment the cartridge is further operable for dispensing between 0 and 100 picoliters.

In another embodiment the cartridge is further operable for dispensing between 0 and 500 picoliters.

In another embodiment the cartridge is further operable for dispensing between 0 and 1 nanoliters.

In another embodiment the cartridge is further operable for dispensing between 0 and 5 nanoliters.

In another embodiment the cartridge is further operable for dispensing between 0 and 10 nanoliters.

In another embodiment the cartridge is further operable for dispensing between 0 and 50 nanoliters.

In another embodiment the cartridge is further operable for dispensing between 0 and 100 nanoliters.

In another embodiment the cartridge is further operable for dispensing between 0 and 500 nanoliters.

In another embodiment the cartridge is further operable for dispensing between 0 and 1 microliters.

In another embodiment the cartridge is further operable for dispensing between 0 and 5 microliters.

In another embodiment the cartridge is further operable for dispensing between 0 and 10 microliters.

In another embodiment the cartridge is further operable for dispensing between 0 and 50 microliters.

In another embodiment the cartridge is further operable for dispensing between 0 and 100 microliters.

In another embodiment the cartridge is further operable for dispensing between 0 and 500 microliters.

In another embodiment the cartridge is further operable for dispensing between 0 and 1 milliliters.

In another embodiment the cartridge is further operable for dispensing between 0 and 5 milliliters.

In another embodiment the cartridge is further operable for dispensing between 0 and 10 milliliters.

In another embodiment the cartridge is further operable for dispensing between 0 and 50 milliliters.

In another embodiment the cartridge is further operable for dispensing between 0 and 100 milliliters.

In another embodiment the cartridge is further operable for dispensing between 0 and 500 milliliters.

In another embodiment the cartridge is further operable for dispensing a micro-fluidic volume of the fluid.

In another embodiment the cartridge further comprises the fluid.

In another embodiment the fluid is any one of the following: a solution, a suspension, an emulsion, and a dispersion with an acid, neutral, or basic pH-value.

In another embodiment the fluid comprises any one of the following: a salt, a polymer, a protein, a preservative, a reagent, magnetic particles, latex particles, a blood grouping reagent, an immune agent, an antibody, an enzyme, a co-enzyme, a recombinant protein, a virus isolate, a detergent, a virus, nano particles, and combinations thereof.

In another embodiment the fluid can act as a stabilizer, a buffer, a reagent, a preservative, a solvent, and combinations thereof.

In another embodiment the fluid can comprise a biological component. A 'biological component' as used herein encompasses a sample that comprises material generated by a biological system. The biological component may for example be, but is not limited to, blood, urine, plasma, serum, tissue, saliva, swabs, stool, or another biological product dissolved in a fluid.

In another aspect, the present disclosure provides for an automatic analyzer for analyzing a biological sample. The automatic analyzer is operable for holding a cartridge according to any one of the preceding embodiments. The automatic analyzer is operable for dispensing the fluid using the cartridge. The cartridge may in one example have a dispenser or pump that is controlled or actuated by the automatic analyzer. In another example the cartridge provides the fluid to a dispenser or pump incorporated into the automatic analyzer.

In one example the automatic analyzer may be operable for holding the cartridge in an operating position.

In another embodiment the automatic analyzer comprises the cartridge.

Although the embodiments of the present disclosure are not limited to specific advantages or functionality, it is understood that one or more of the aforementioned embodiments of the disclosure may be combined as long as the combined embodiments are not mutually exclusive.

In order that the embodiments of the present disclosure may be more readily understood, reference is made to the following examples, which are intended to illustrate the disclosure, but not limit the scope thereof.

FIG. 1 illustrates an example of a cartridge 100. The cartridge comprises a rigid portion 102 and a flexible bladder 104. The rigid portion is shown as having an axis of symmetry 106. It should be noted that in not all examples does the rigid body 102 have an axis of symmetry 106. The rigid portion 102 has an outlet 108. In this example the outlet 108 is seen as connecting with a nozzle 110. However, the nozzle is representative. Different examples of the cartridge 100 may have a nozzle 110 and/or a valve, and/or a pump for removing fluid from the cartridge 100. The rigid portion 102 has an opening 114. The dashed line 112 indicates the location of the opening 114. The flexible bladder 104 is attached to the rigid portion 102 and seals the opening 114. The rigid portion 102 has an inner cavity 116 that is defined by the outlet 108, the opening 114, and an inner cavity surface 118. The flexible bladder 104 may extend out beyond the opening 114. When the flexible bladder extends beyond the opening 114 it forms a bladder volume 120. The space enclosed by the rigid portion 102 and the flexible bladder 104 is a fluid chamber 122 for receiving fluid 123. The fluid chamber 122 may also be considered to be made up of the inner cavity 116 and the bladder volume 120.

In FIG. 1 and the following examples, the cartridge 100 is shown as being in an operating position where the outlet is at the bottom of the rigid portion 102 and the flexible bladder 104 is shown as being mounted at the top of the rigid portion 102. The nozzle 110 or equivalent component for dispensing the fluid 123 is then at the lowest point of the cartridge 100. This orientation of the cartridge 100 in this FIG. 1 and the other FIGS. is intended only as an example. The cartridge 100 can be placed in any orientation and a pump or the flexible bladder 104 may be used to force fluid from the cartridge 100. For example, the cartridge 100 may be orientated such that the axis 106 shown in FIG. 1 is horizontal.

Figure 2:
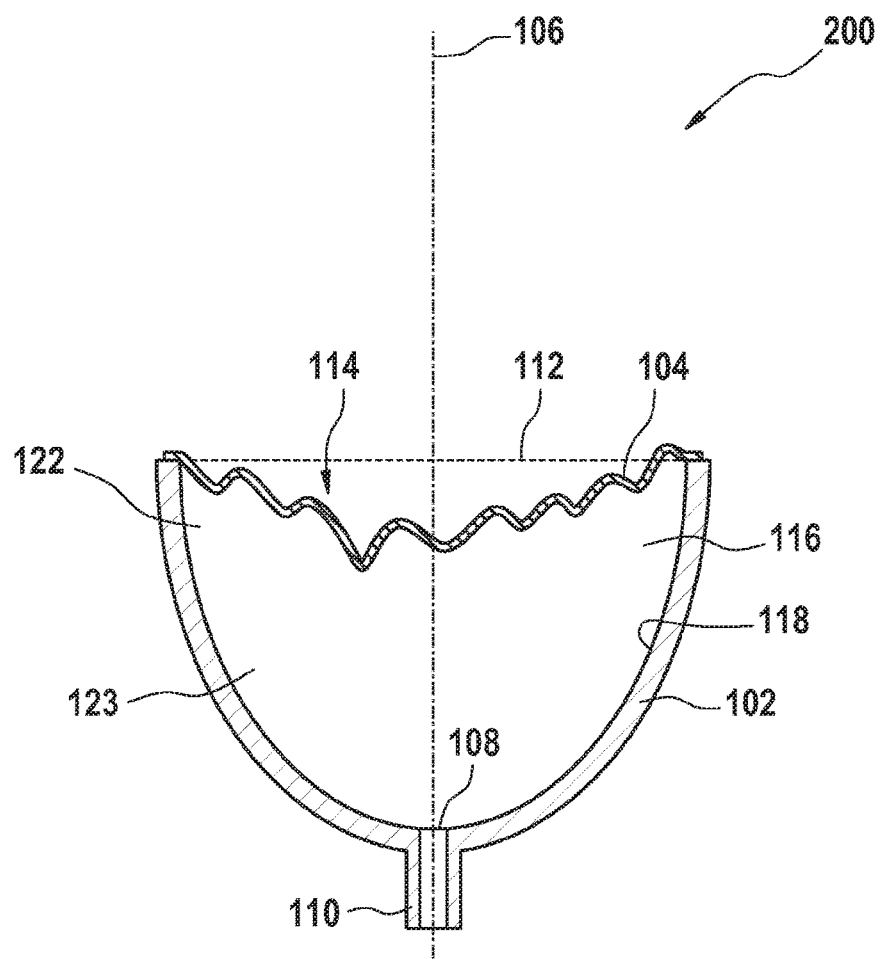

FIG. 2 shows a cartridge 200 similar to that shown in FIG. 1. In this example the flexible bladder 104 is inelastic. As fluid is drained from the cartridge the flexible bladder 104 collapses towards the inner cavity surface 118. The fluid chamber 122 is again filled with fluid 123. However, the flexible bladder 104 has collapsed such that the fluid chamber 122 is defined by the flexible bladder 104 and the inner cavity surface 118. A portion of the inner cavity 116 is no longer filled with fluid 123.

Figure 3:
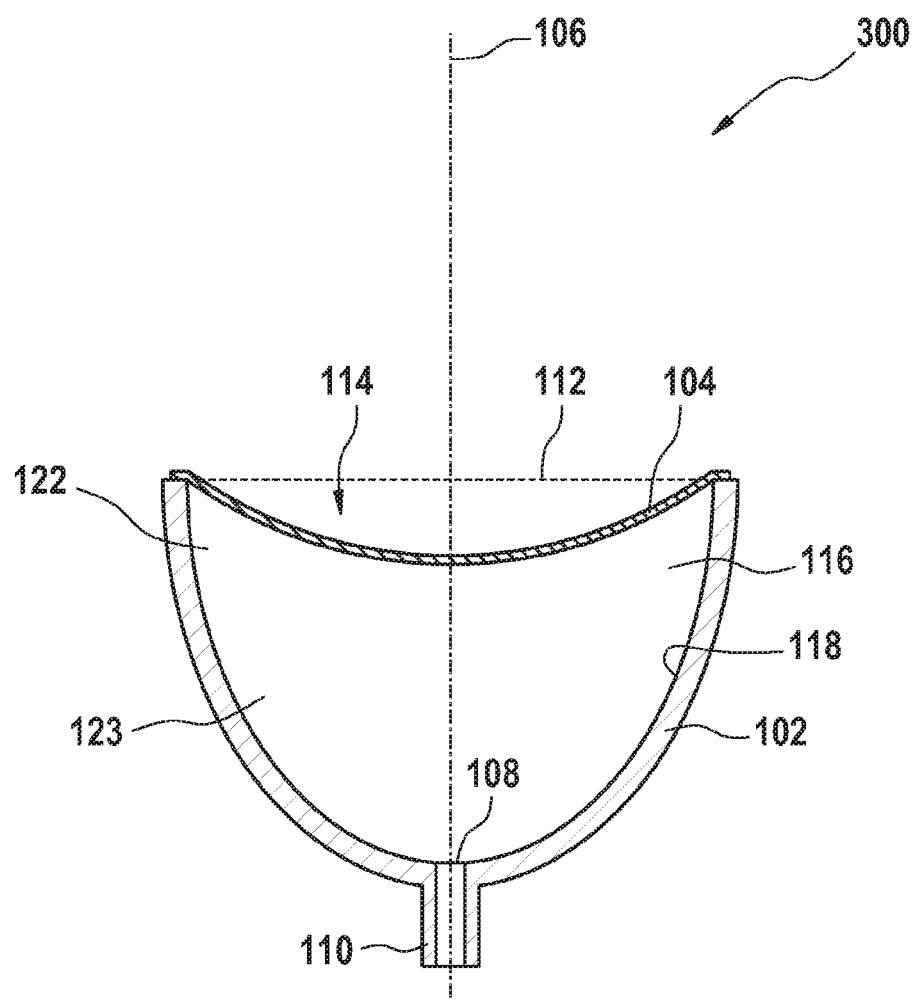

FIG. 3 shows a further example of a cartridge 300. The example shown in FIG. 3 is similar to that shown in FIGS. 1 and 2. However, in this example the flexible bladder 104 is elastic. It can be seen in this FIG. 3 that as the fluid 123 is drained from the fluid chamber 122 that the flexible bladder 104 will stretch towards the inner cavity surface 118.

Figure 4:
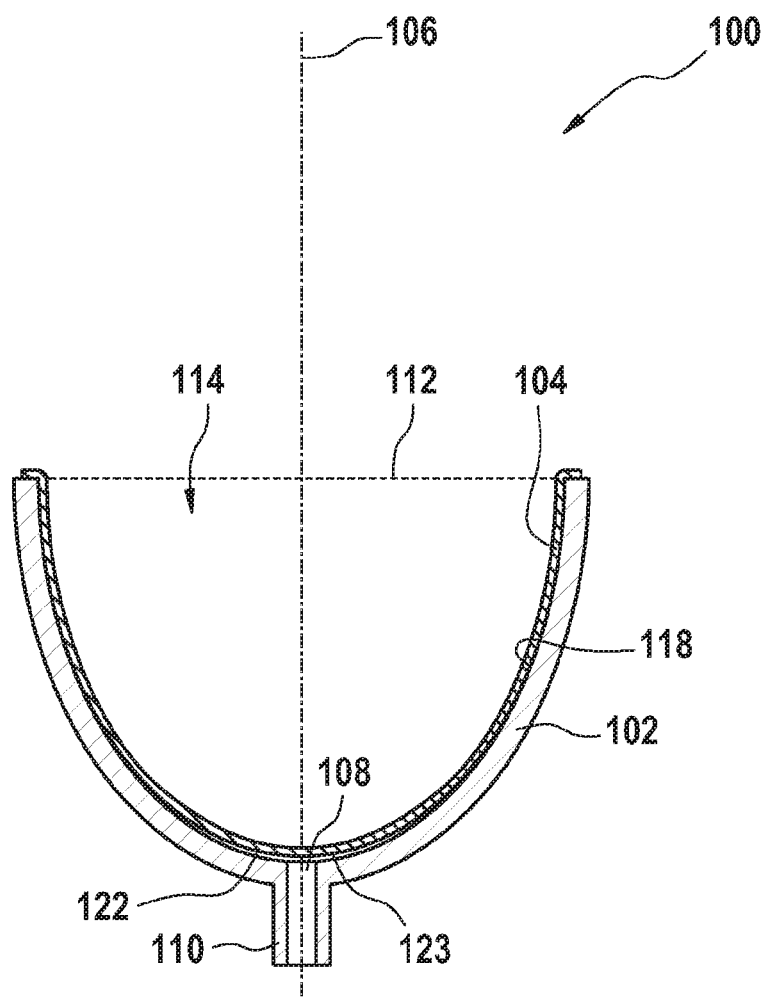

FIG. 4 shows a further view of the cartridge 100 in FIG. 1. In the example shown in FIG. 4 the fluid 123 has been completely or almost completely drained from the cartridge 100. The flexible bladder 104 is shown as covering the inner cavity surface 118. In the example shown in FIG. 4 the flexible bladder 104 may be elastic and may be stretching to cover the inner cavity surface 118 or it may be an inflexible bladder such as shown in FIG. 2, however the flexible bladder 104 is fitted such that when the fluid 123 is removed from the cartridge 100 the flexible bladder 104 fits and covers the inner cavity surface 118.

Figure 5:
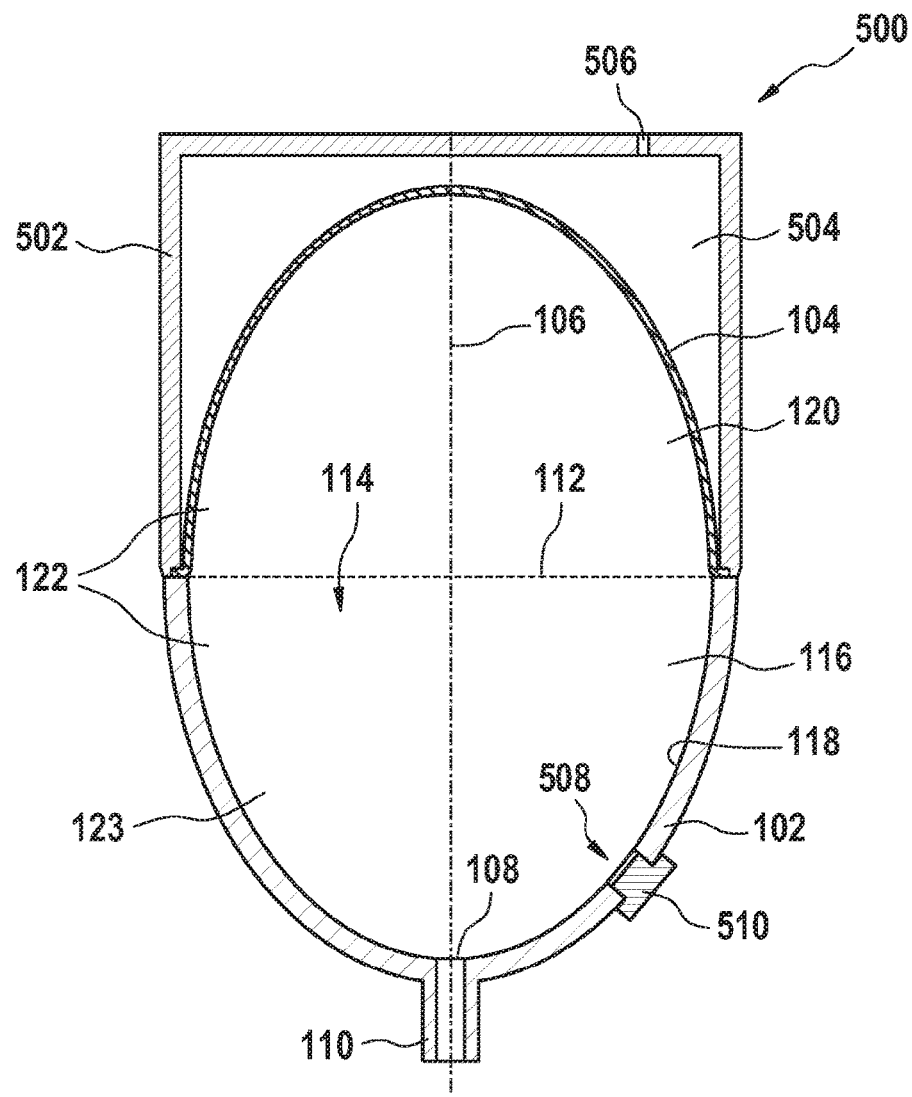

FIG. 5 shows a further example of a cartridge 500. The cartridge 500 shown in FIG. 5 is similar to that shown in FIGS. 1-4. The cartridge 500 is shown as additionally comprising a cap 502. The cap 502 is attached to the rigid portion 102. The cap 502 forms a cap cavity 504. In this particular example the dotted line 112 represents a division between the cap cavity 504 and the inner cavity 116. The flexible bladder 104 is shown as expanding into the cap cavity 504. The cap 502 may serve several functions. In one aspect it may protect the flexible bladder 104. The cap 502 may also be operable for providing mechanical support to the cartridge 500, for example by providing at least partially a mounting for connecting to a device such as an automatic analyzer. The cap 502 may also limit the expansion of an elastic flexible bladder 104. The cap 502 is shown as further comprising a gas inlet 506. The gas inlet 506 may be used as a vent or for pressurizing the cap cavity 504. The gas inlet 506 provides a means for equalizing the pressure of the cap cavity 504 when fluid 123 is removed from the cartridge 500. Pressurizing the gas inlet 506 may be beneficial because it may enable almost all of the fluid 123 to be forced out of the cartridge 500. The example shown in FIG. 5 has a cartridge 500 with a fluid inlet 508. The fluid inlet 508 is shown as being covered with a seal 510. The fluid inlet 508 and seal 510 are intended to be representative. Different sorts and types of sealable or re-sealable inlets may be used. The fluid inlet 508 provides a convenient means of filling the cartridge 500 with fluid 123.

Figure 6:
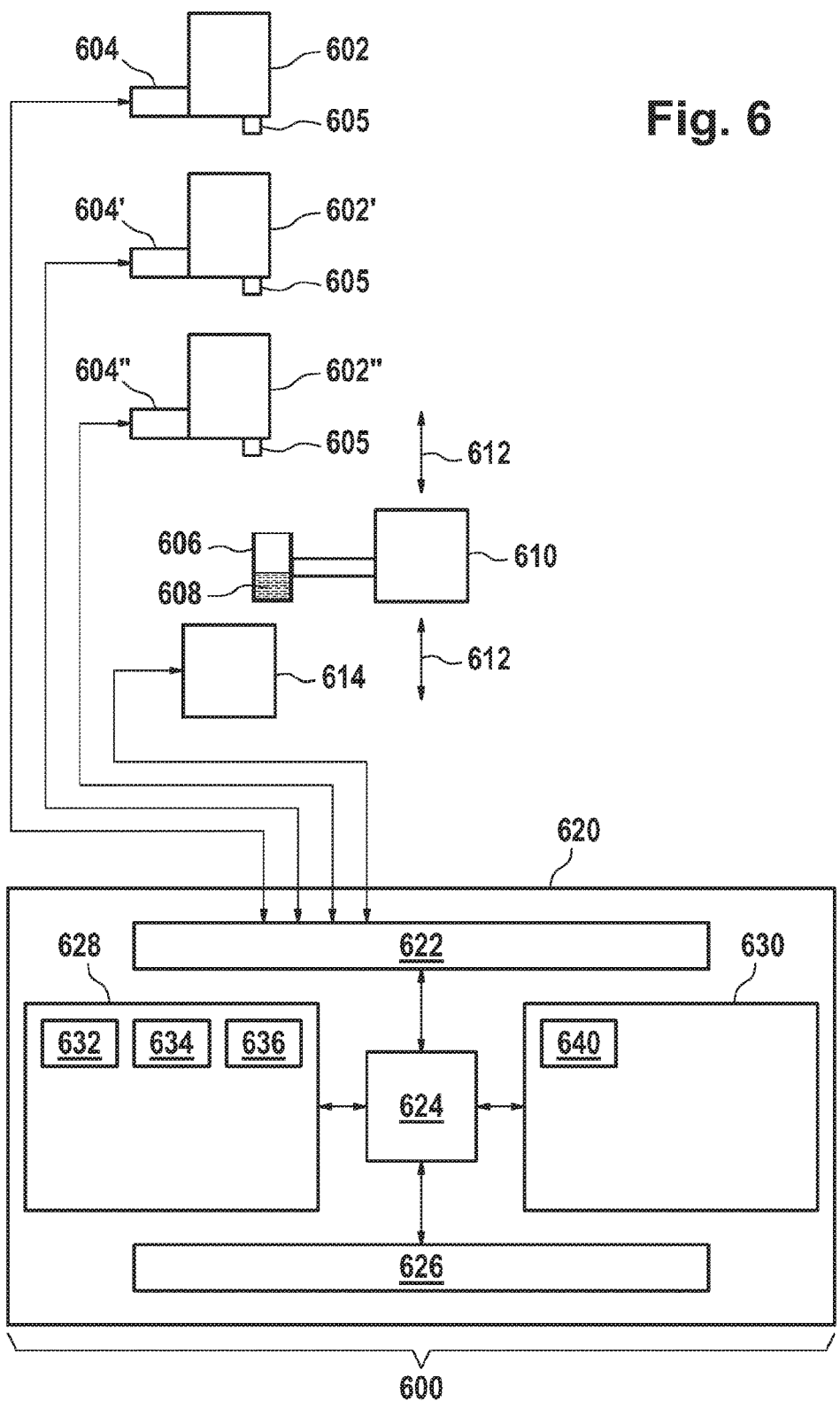
FIGS. 6, 25, 27 and 29 each illustrates an example of an automatic analyzer in accordance with an embodiment of the present disclosure.

FIG. 6 illustrates an automatic analyzer 600 according to an embodiment of the disclosure. This automatic analyzer is shown as having three cartridges 602, 602' and 602". There is an actuator assembly 604 connected to cartridge 602. There is an actuator assembly 604' attached to cartridge 602'. There is an actuator assembly 604" attached to cartridge 602". The actuators 604, 604', 604" are for actuating a dispenser 605 for each of the cartridges 602, 602', 602". The dispenser 605 may be incorporated into the cartridges 602, 602', 602" or it may be a component of the automatic analyzer 600.

The automatic analyzer 600 is shown as having a relative movement means 610, which provides relative movement 612 between a sample holder 606 and the cartridges 602, 602' and 602". The sample holder 606 is shown as containing a biological sample 608. The cartridges 602, 602', 602" may be used to add one or more fluids to the biological sample 608. The automatic analyzer 600 may optionally comprise a measurement system 614. The measurement system 614 may comprise one or more sensors for measuring a physical quantity or physical property of the biological sample 608. For example, the measurement system 614 may for example comprise, but is not limited to, an NMR system, an optical transmission or reflectance measurement system, an electrochemical or optical sensor, a pH meter, a camera system or a chromatography system. The relative movement means 610 is also operable for moving the sample holder 606 to the measurement system 614.

The arrangement of the cartridges 602, 602', 602" and the measurement system 614 is representative. The measurement system 614 may be alternatively also a part of the sample holder 606. In some embodiments the sample holder 606 may remain in a fixed position and the cartridges 602, 602', 602" may move. The actuation systems 604, 604', 604" and the measurement system 614 are shown as being connected to a hardware interface 622 of a computer system 620. The relative movement means 610 may also be connected to a hardware interface 622 of a computer system 620 (not shown here). The computer system 620 functions as a controller for the automatic analyzer 600. The computer system 620 is further shown as containing a processor 624, which is able to control the operation and function of the automatic analyzer 600 using the hardware interface 622. The processor 624 is shown as further being connected to a user interface 626, computer storage 628 and computer memory 630. The computer storage 628 is shown as containing an analysis request 632. The analysis request 632 contains a request to analyze the biological sample 608.

The computer storage 628 is shown as further containing sensor data 634 received from the measurement system 614. The computer storage 628 is shown as further containing an analysis result 636, which was determined using the sensor data 634. The computer memory 630 contains a control module 640. The control module 640 contains computer executable code that enables the processor 624 to control the operation and function of the automatic analyzer 600. For instance, the control module 640 may use the analysis request 632 to generate commands to generate and send to the actuation systems 604, 604', 604", the measurement system 614 and the relative movement system 610. The control module 640 may also generate the analysis result 636 using the sensor data 634.

Figure 7:
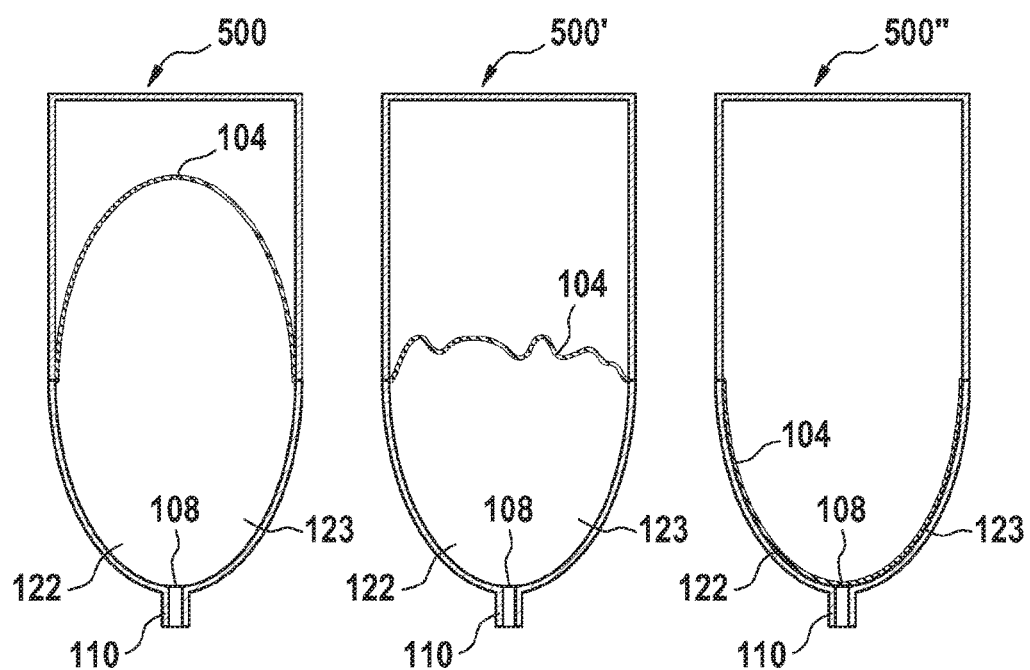

FIG. 7 shows the cartridge 500 of FIG. 5 in several different states. The view labeled 500 shows the cartridge 500 in a fully filled state. The view 500' shows the cartridge 500 partially filled. The view 500" shows the cartridge 500 when the fluid has been drained completely from the cartridge.

Figure 8:
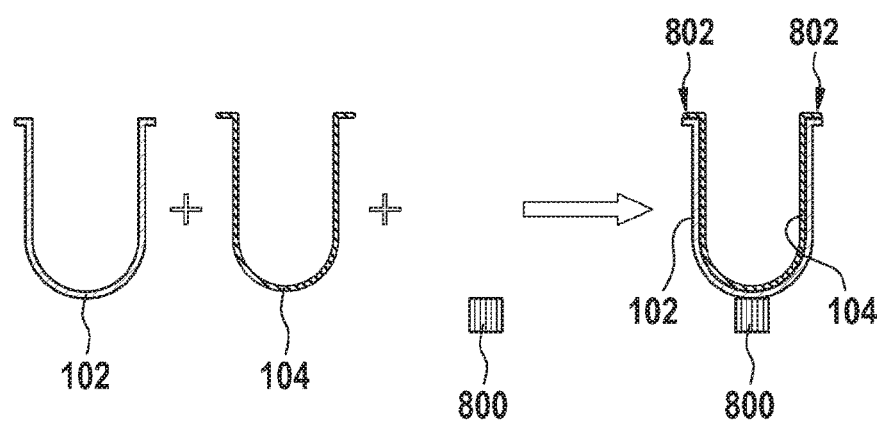

FIG. 8 illustrates in a schematic view several components used to construct an example of a cartridge. On the left are shown components for making a cartridge. There is a rigid portion 102 and a flexible bladder 104. This is combined in this example with a dispenser 800. On the right these components are assembled. The flexible bladder 104 has been mounted in the rigid portion 102 and has been sealed at points 802. The dispenser 800 is shown as being attached to the rigid portion 102.

Figure 9:
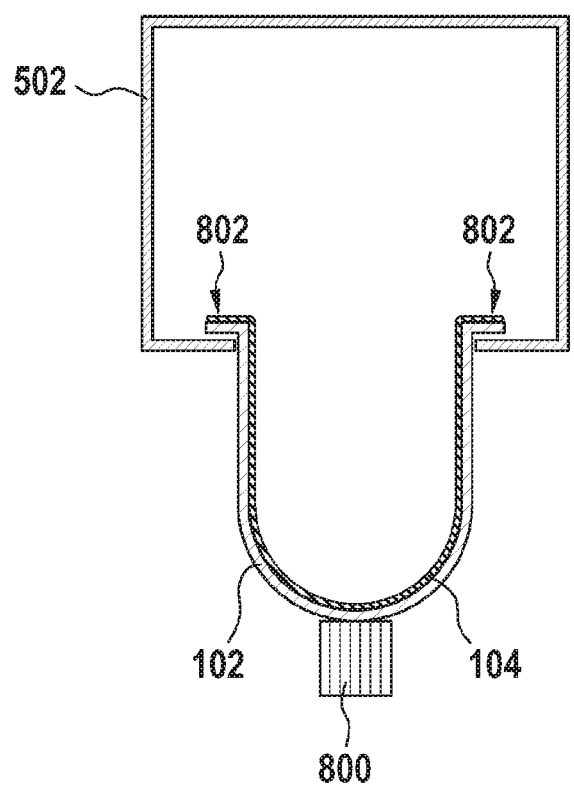

FIG. 9 shows a variation of the cartridge that was assembled in FIG. 8. In this example a cap 502 has been mounted or attached to the rigid portion 102. The flexible bladder 104 may extend into the cap 502. Although it is not shown in FIG. 9 there may be a gas inlet to enable pressure to equalize within the cap 502.

Figure 10:
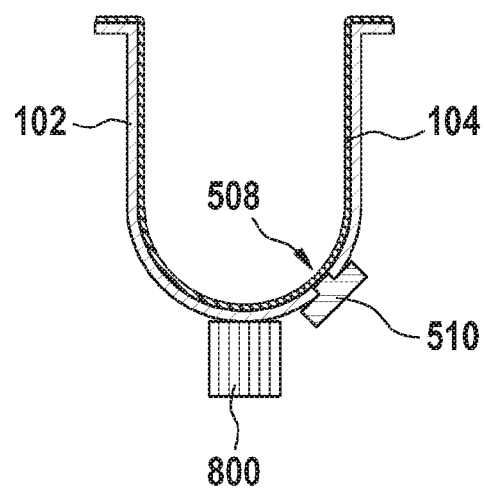

FIG. 10 shows a further example of a cartridge similar to that shown in FIG. 8. In this example there is a fluid inlet 508 on the rigid portion 102, which is closed by a seal 510.

FIGS. 11-15 illustrate several different shapes of the cartridges.

Figure 11:
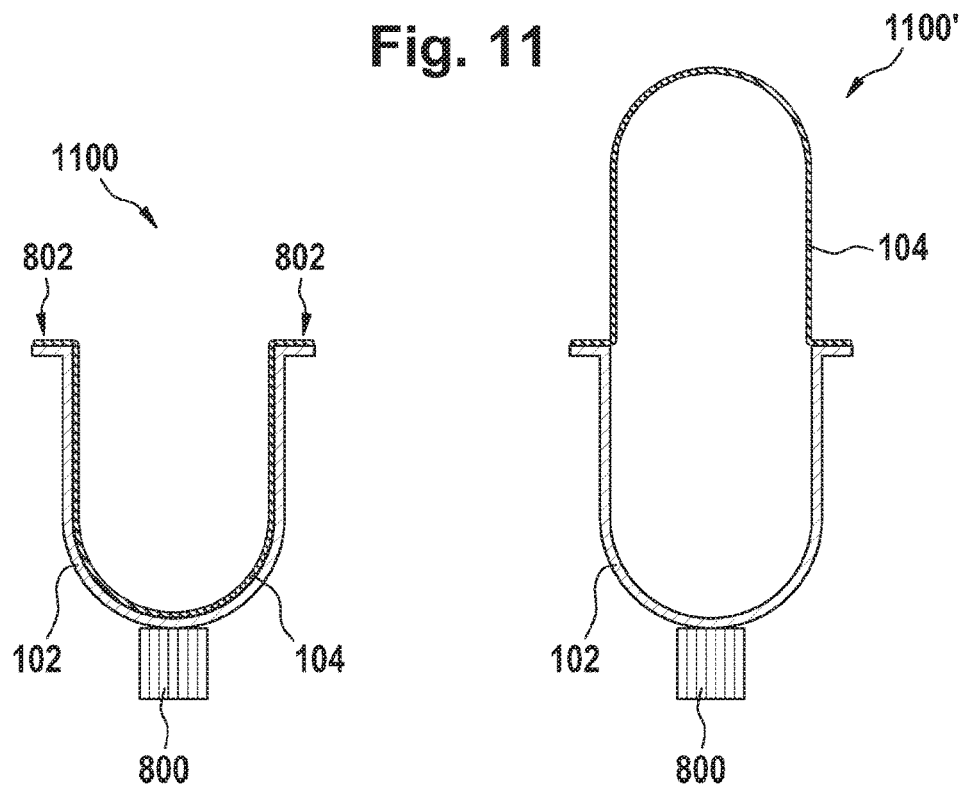

In FIG. 11, a cartridge is shown in an empty state 1100 and a filled state 1100'. In the example shown in FIG. 11, the rigid portion 102 is ball-shaped.

Figure 12:
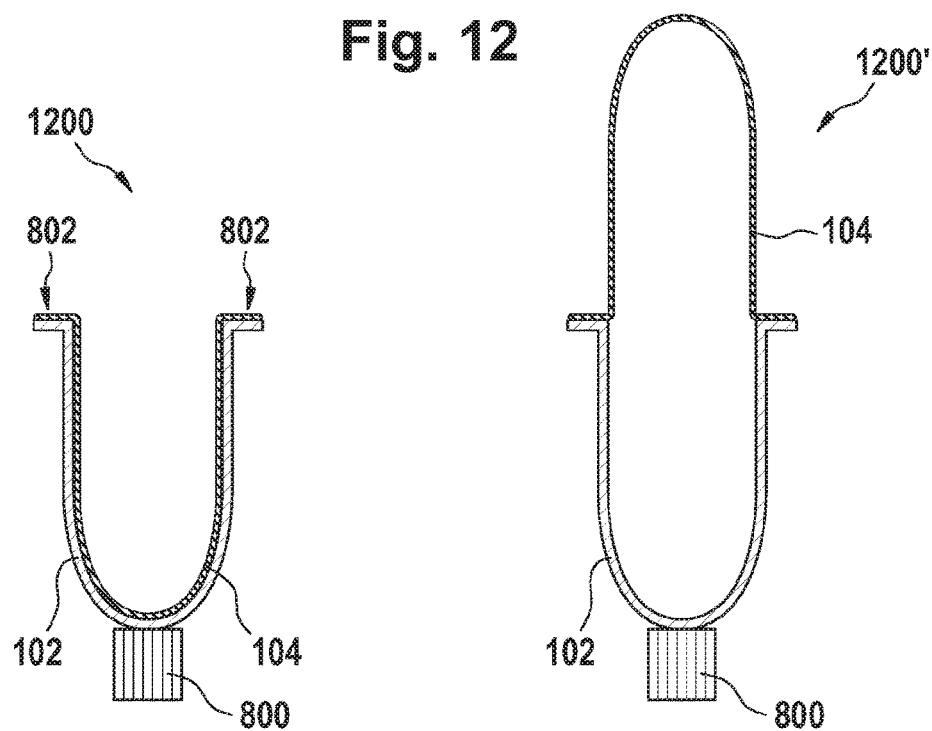

In FIG. 12, a cartridge is shown in an empty state 1200 and a filled state 1200'. In this case the rigid portion 102 is oval-shaped.

Figure 13:
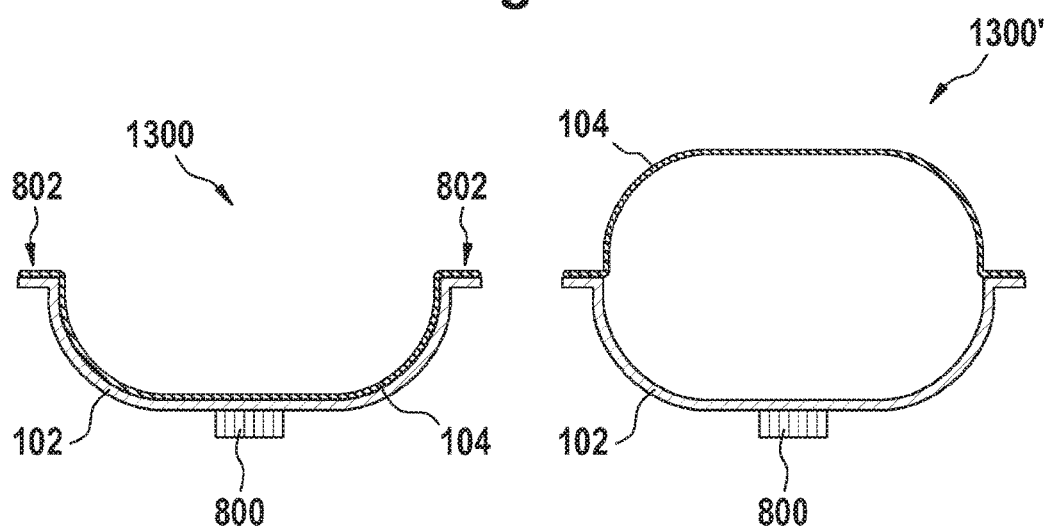

FIG. 13 shows a cup-shaped rigid portion 102 that is part of a cartridge in an empty state 1300 and a filled state 1300'.

Figure 14:
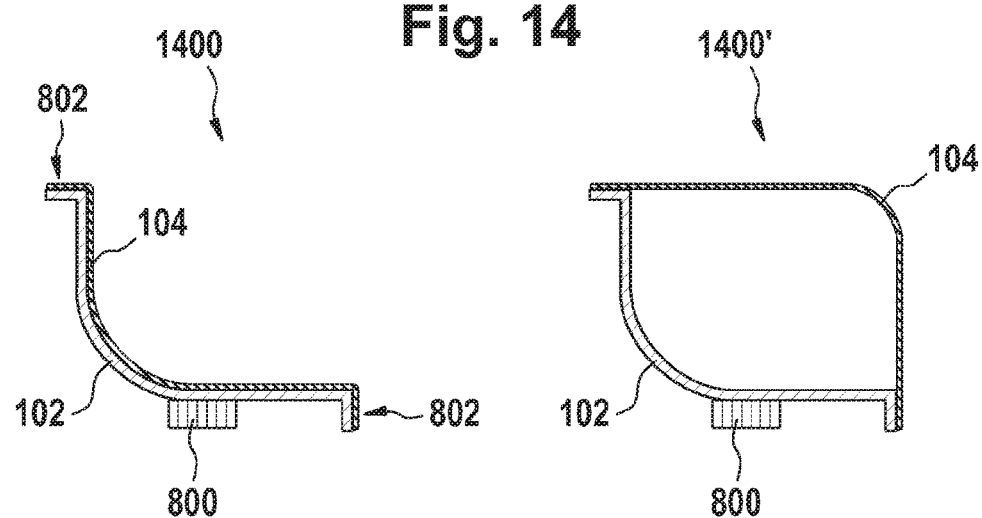

FIG. 14 shows a cartridge in an empty state 1400 and a filled state 1400' where the rigid portion 102 is rectangular-shaped ("L"-shaped).

The views shown in FIGS. 11-14 are cross-sectional.

Figure 15:
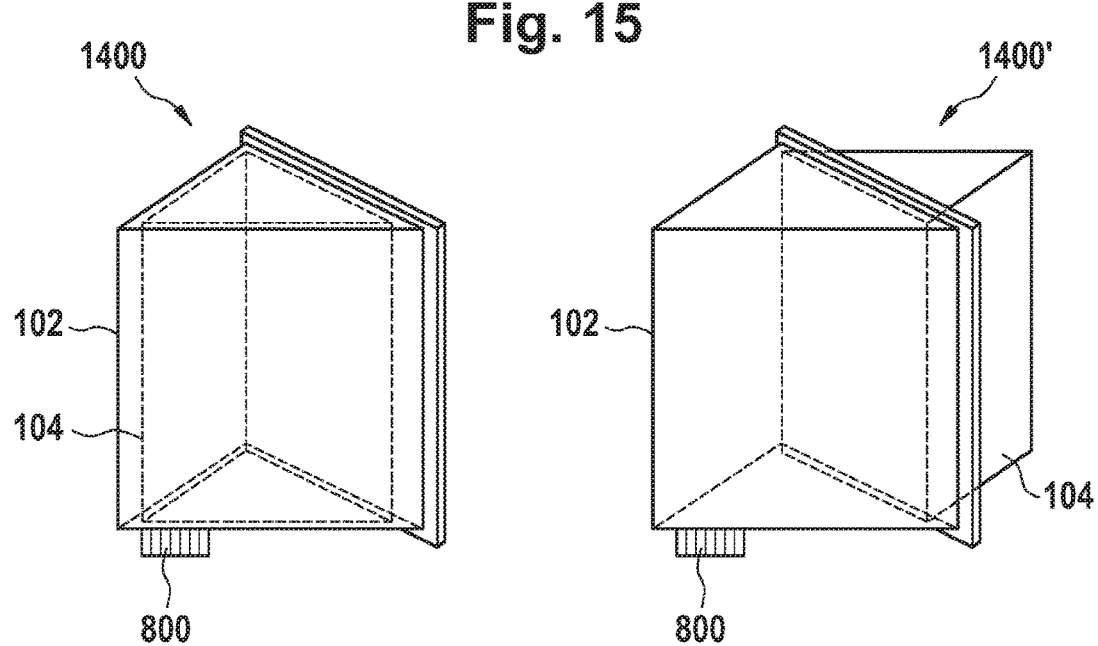

FIG. 15 shows a cartridge in an empty state 1400 and in a filled state 1400' in a perspective view, in accordance with another embodiment of the disclosure.

Figure 16:
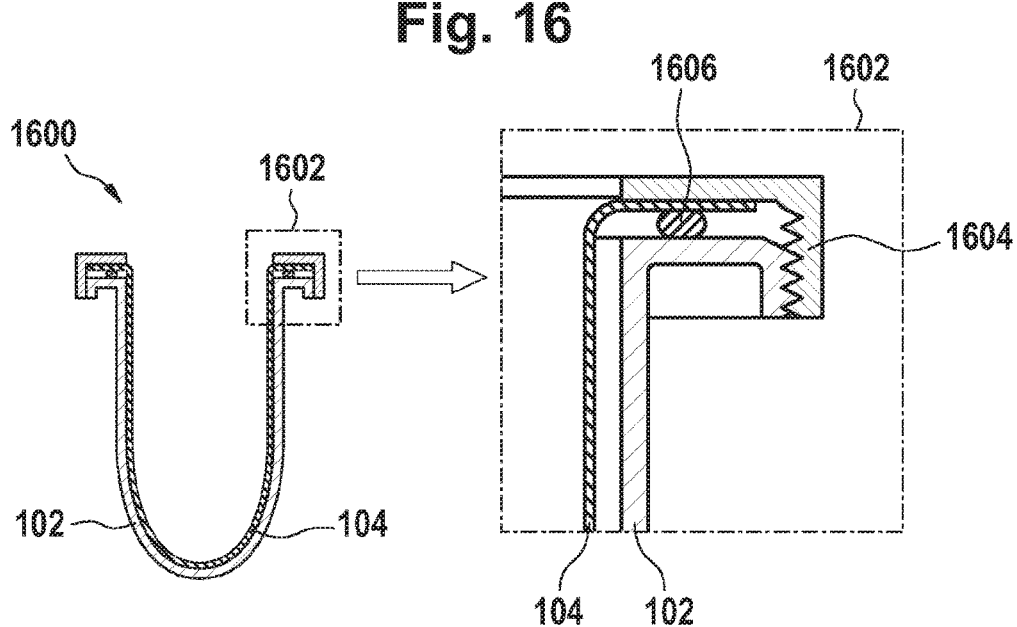

FIG. 16 shows a further example of a cartridge 1600. In FIG. 16, one method of attaching the flexible bladder 104 to the rigid portion 102 is shown. Box 1602 is a region that shows expanded detail. In this example a screw cap 1604 is used to compress the flexible bladder 104 against an elastic seal 1606, which in turn compresses against the rigid portion 102. The elastic seal 1606 is compressed and forms a seal against the fluid.

Figure 17:
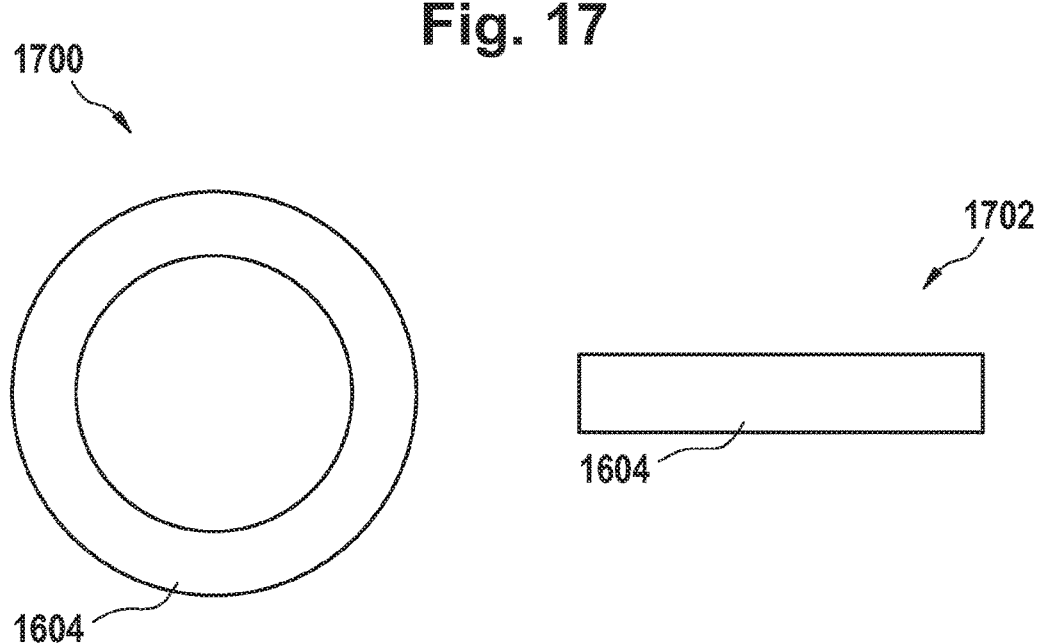
FIG. 17 illustrates an example of a screw cap in accordance with an embodiment of the present disclosure.

FIG. 17 shows a top view 1700 and a side view 1702 of the screw cap 1604.

Figure 18:
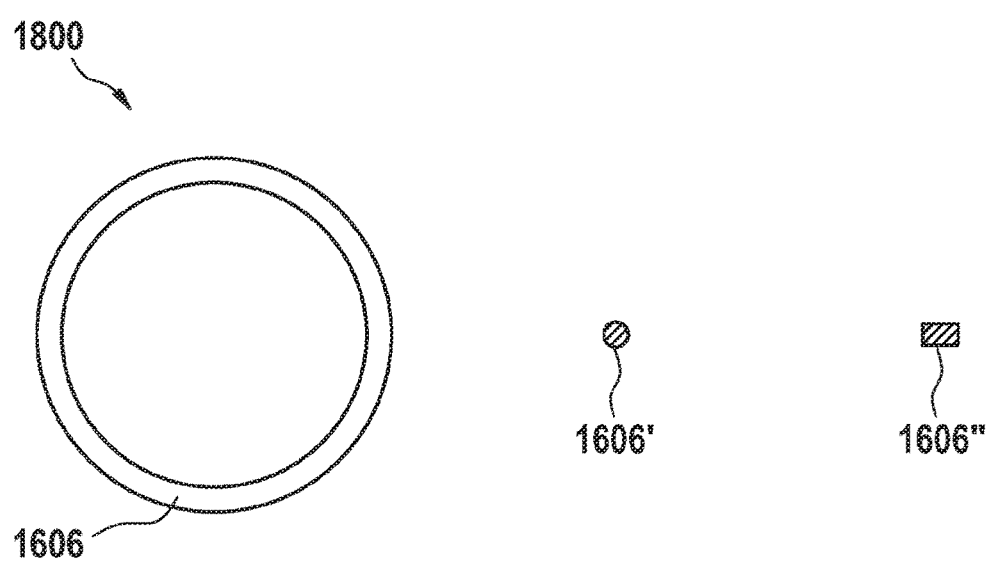
FIG. 18 illustrates an example of an elastic seal in accordance with an embodiment of the present disclosure.

FIG. 18 shows a top view 1800 and a side view 1802 of the elastic seal 1606. The elastic seal 1606 is shown as being either an O-ring 1606' or a flat ring 1606".

Figure 19:
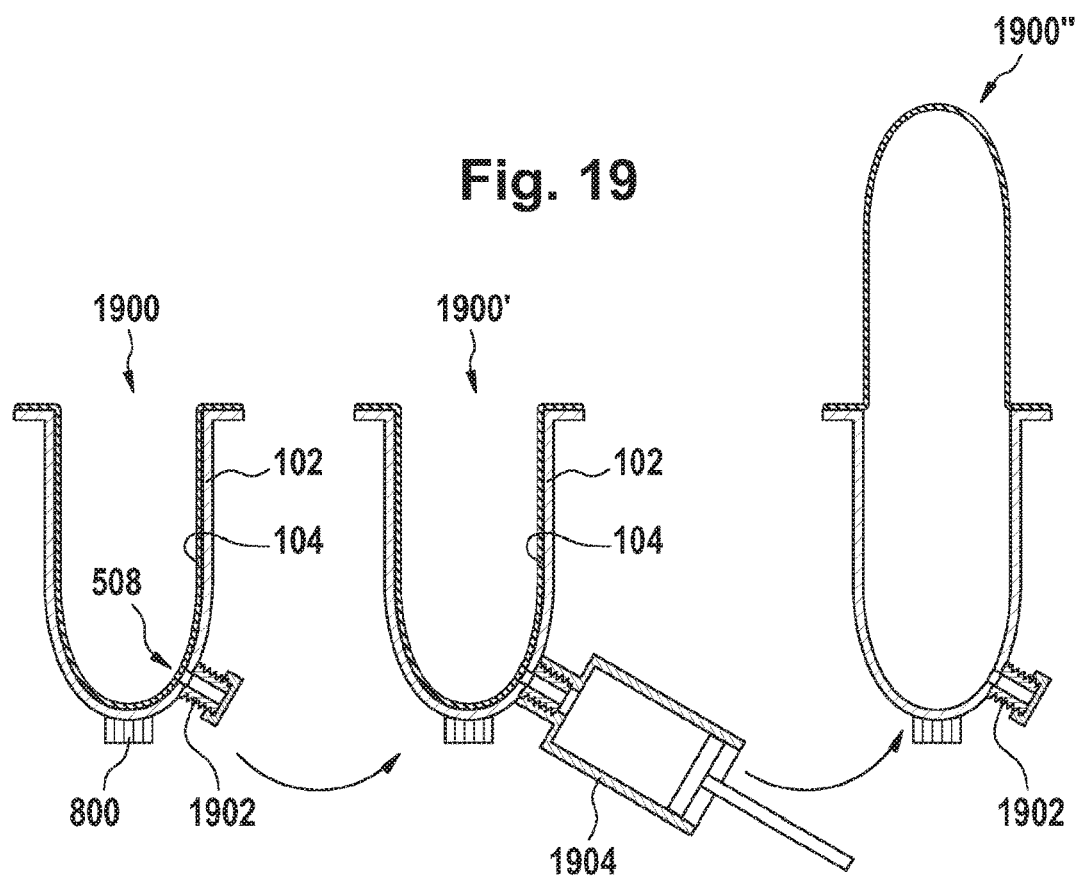

FIG. 19 shows a first view 1900 of a cartridge with a fluid inlet 508. The fluid inlet 508 is shown as being sealed by a luer lock with a cap 1902. View 1900' shows the same cartridge but with a syringe 1904 attached to the luer lock. The syringe 1904 contains the fluid and then may be compressed to force the fluid into the cartridge. View 1900" shows the cartridge in a filled state with the syringe 1904 removed and with the cap in place in the luer lock 1902.

Figure 20:
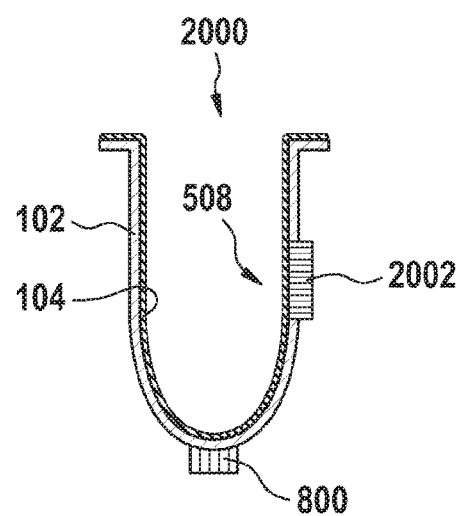

FIG. 20 shows a further example of a cartridge 2000. Cartridge 2000 has a fluid inlet 508 that is sealed by a screw cap 2002.

Figure 21:
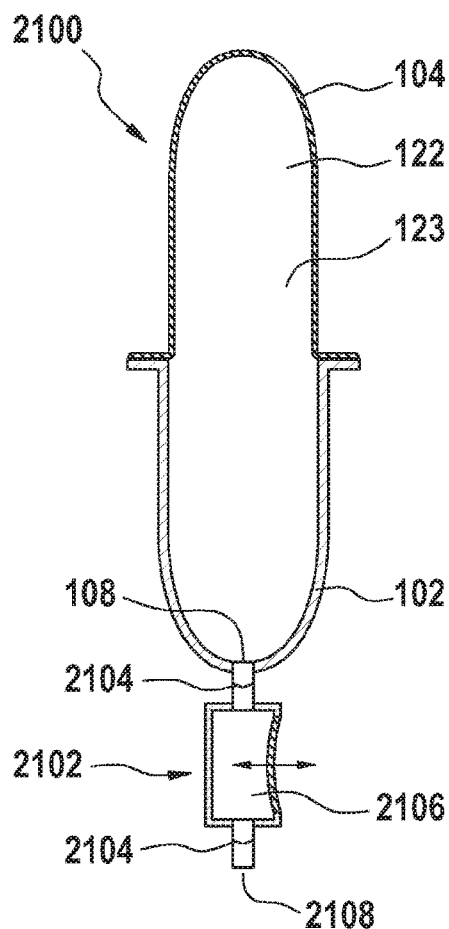

FIG. 21 shows a cartridge 2100 filled with fluid 123 connected to a diaphragm pump 2102. The diaphragm pump 2102 comprises two valves 2104 that may be operated independently, and a compressible volume 2106. The compressible volume 2106 is used in conjunction with the valves to pump fluid out through a nozzle 2108.

Figure 22:
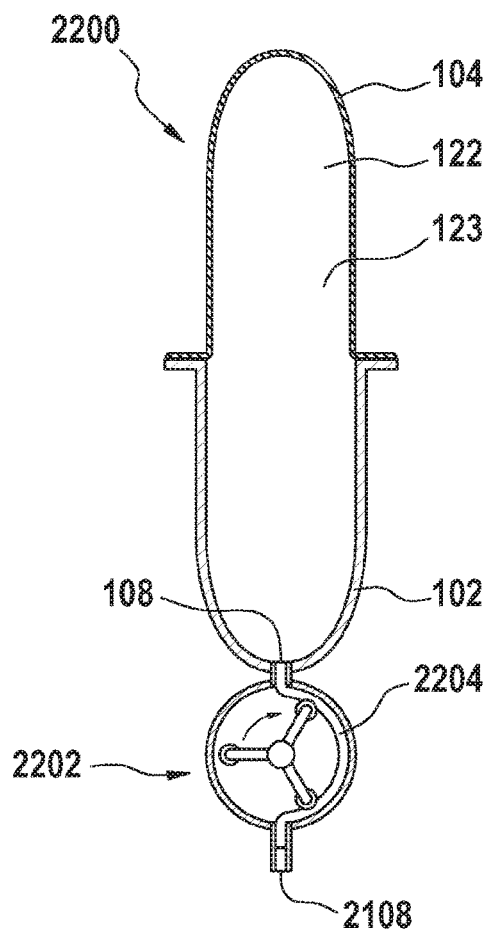

FIG. 22 shows a cartridge 2200 that is connected to a peristaltic pump 2202. The outlet 108 is connected to a tube 2204, which is then connected to a nozzle 2108. The peristaltic pump 2202 compresses a portion of the tube 2204, thereby pumping fluid 123 from the cartridge 2200.

FIG. 23 shows a cartridge 2300 connected to a piston pump 2302.

FIG. 24 shows the piston pump 2302 in greater detail. The piston pump 2302 may be attached to the cartridge 2300 or the piston pump 2302 may be incorporated into the cartridge 2300. The piston pump 2302 is shown in four different views in FIG. 24, 2400, 2402, 2404, 2406. In view 2400 the piston pump 2302 is shown as being connected to the outlet 108. The piston pump 2302 has a rotatable portion 2408. The rotatable portion 2408 may be used to connect the pump 2302 to either the outlet 108 or a nozzle 2108. There is a piston 2410 for pumping. In view 2400 the rotatable portion 2408 is shown as being connected to the outlet 108 and the piston 2410 is fully compressed. Next, in view 2402, the piston 2410 is withdrawn forming a pumping volume 2412 within the rotatable portion 2408. This withdraws fluid 123 from the cartridge 2300. Next, in view 2404, the rotatable portion 2408 is rotated such that the pumping volume 2412 is connected with the nozzle 2108. Then, finally in view 2406, the piston 2410 is compressed forcing the fluid 123 that was in the fluid volume 2412 out through the nozzle 2108.

Figure 25:
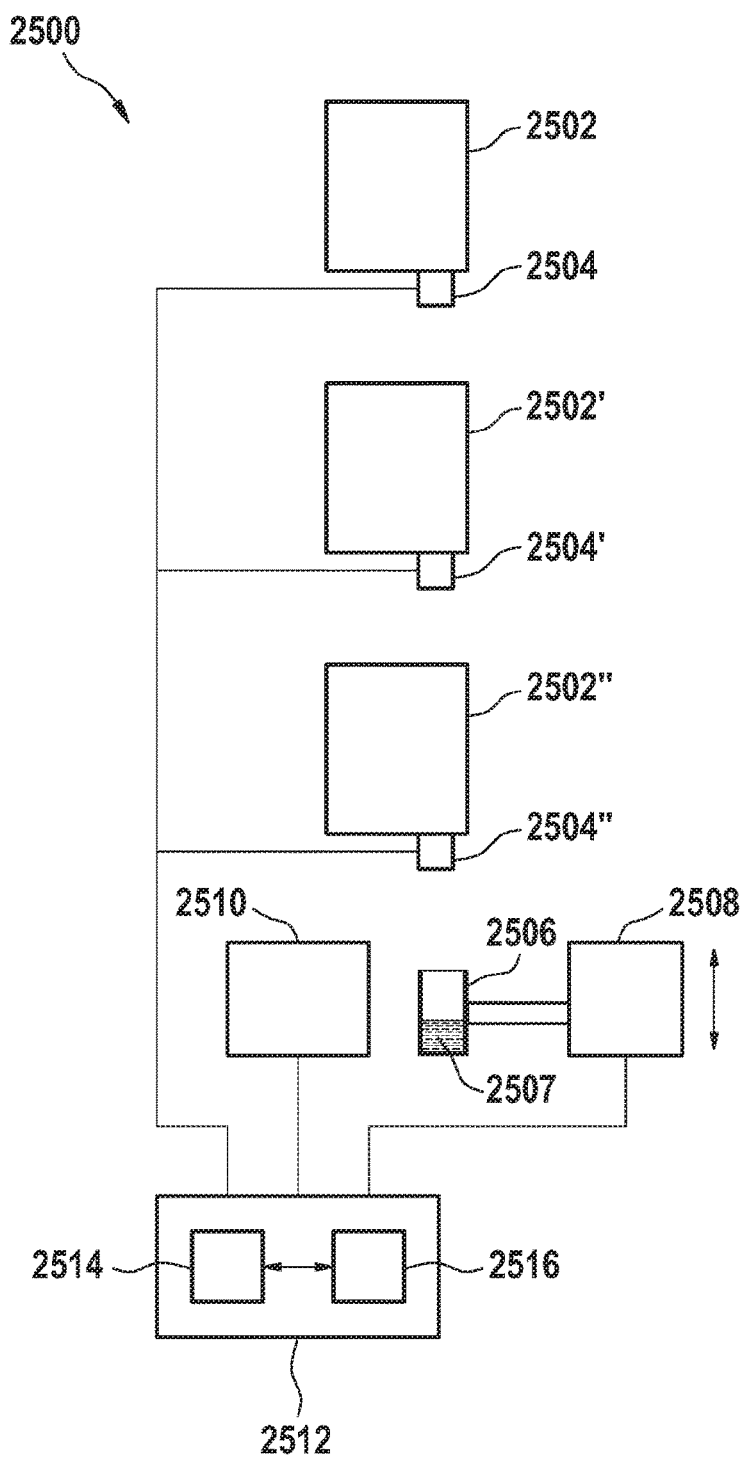

FIG. 25 shows an example of an automatic analyzer 2500. In this automatic analyzer 2500 there are three different cartridges 2502, 2502', 2502". The cartridge may be according to any one of the examples previously illustrated. Attached to each cartridge 2502, 2502', 2502" is a pump. Pump 2504 is attached to cartridge 2502. Pump 2504' is attached to cartridge 2502' and pump 2504" is attached to cartridge 2502". There is a sample holder 2506, which contains a sample 2507. A translation mechanism 2508 may move the sample holder 2506 such that each of the cartridges 2502, 2502', 2502" may dispense fluid into the sample holder 2506 to mix it with the sample 2507. The automatic analyzer 2500 is also shown as having a measurement unit 2510 for performing the measurement on the sample 2507 after it has been mixed with fluid or fluids from the cartridges 2502, 2502', 2502".

FIG. 25 is further shown as containing a controller 2512. The controller 2512 contains a memory 2514 that contains machine-executable instructions. The controller 2512 further contains a processor 2516 for executing the machine-executable instructions stored in the memory 2514. The controller 2512 is connected to each of the pumps 2504, 2504', 2504" and also to the translation mechanism 2508 and the measurement unit 2510. The processor 2516 is then able to control the operation and function of the automatic analyzer 2500.

Figure 26:
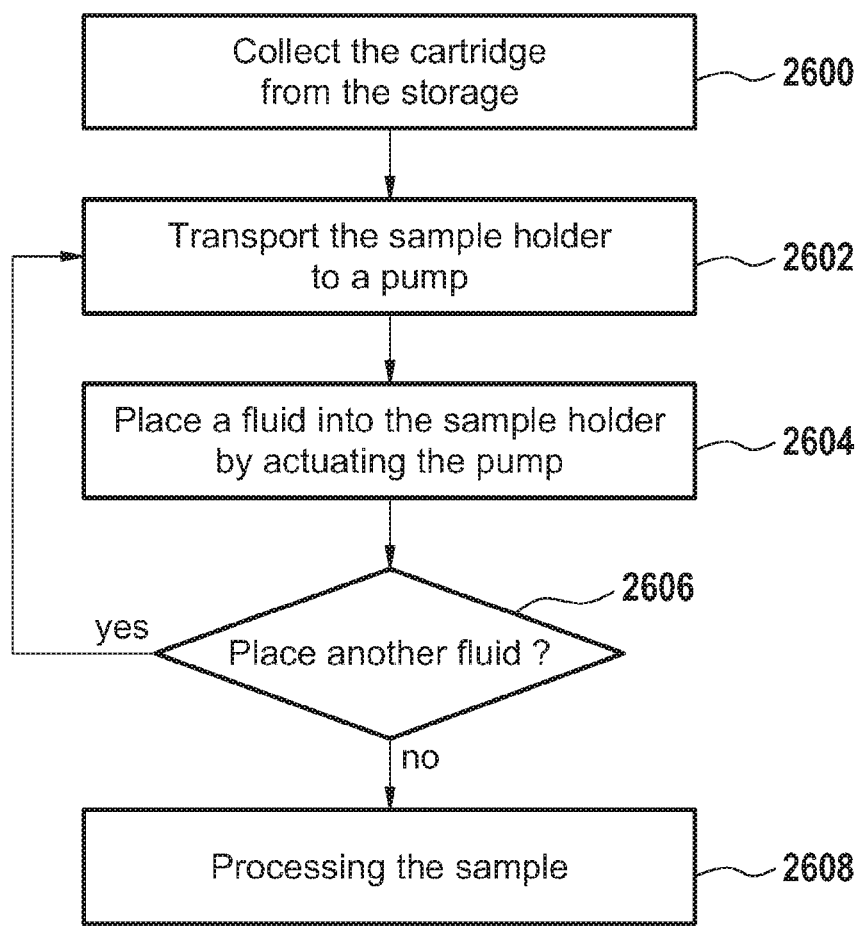

FIG. 26 shows a flowchart that illustrates a method of using the automatic analyzer 2500 of FIG. 25. First, in step 2600, the cartridges 2502, 2502', 2502" may be collected or brought in from storage. Next, in step 2602, the sample holder is transported to one of the pumps 2504, 2504', or 2504". Next, in step 2604, a fluid is mixed or placed into the sample 2507 that is stored in the sample holder 2506 by actuating the pump 2504, 2504', 2504" that the sample holder 2506 has been moved to. Block 2606 is a decision block that has the question to place another fluid into the sample holder 2506. If the answer is yes then the method goes to step 2602 and the sample holder 2506 is moved in front of a different pump. If the answer is no then the sample is processed in block 2608. The method may also include making a measurement with the measurement unit 2510.

Figure 27:
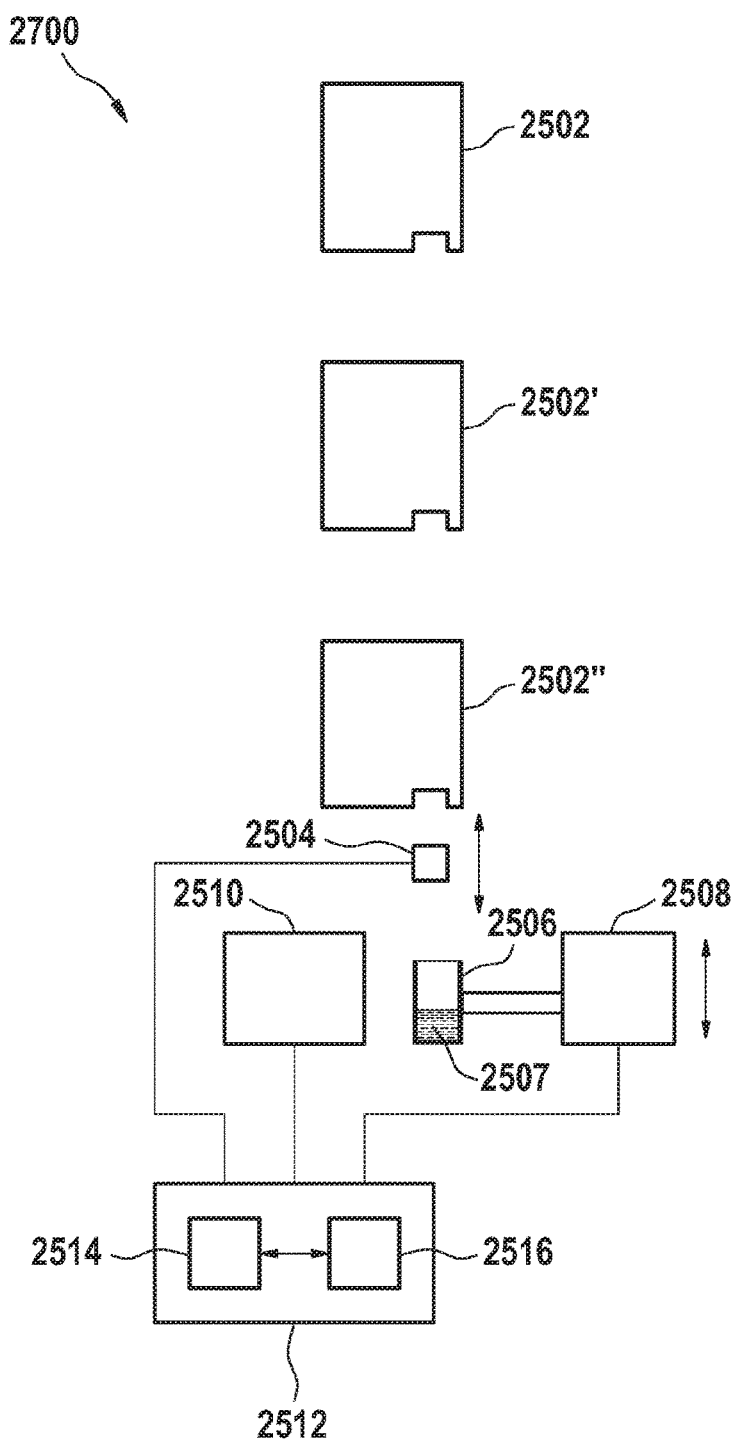

FIG. 27 shows a further example of an automatic analyzer 2700. In this example there are again three cartridges 2502, 2502' and 2502". However, in this example the pump 2504 is not attached to any one particular cartridge 2502, 2502', 2502". The functioning of the automatic analyzer 2700 is similar to that in FIG. 25 except the translation mechanism 2508 is also able to move the pump 2504 from cartridge-to-cartridge as it also moves the sample holder 2506. There for instance may be a coupling that enables the pump 2504 to attach to the different cartridges 2502, 2502', 2502". FIG. 27 contains also a controller 2512 that is analogous to the controller 2512 shown in FIG. 25.

Figure 28:
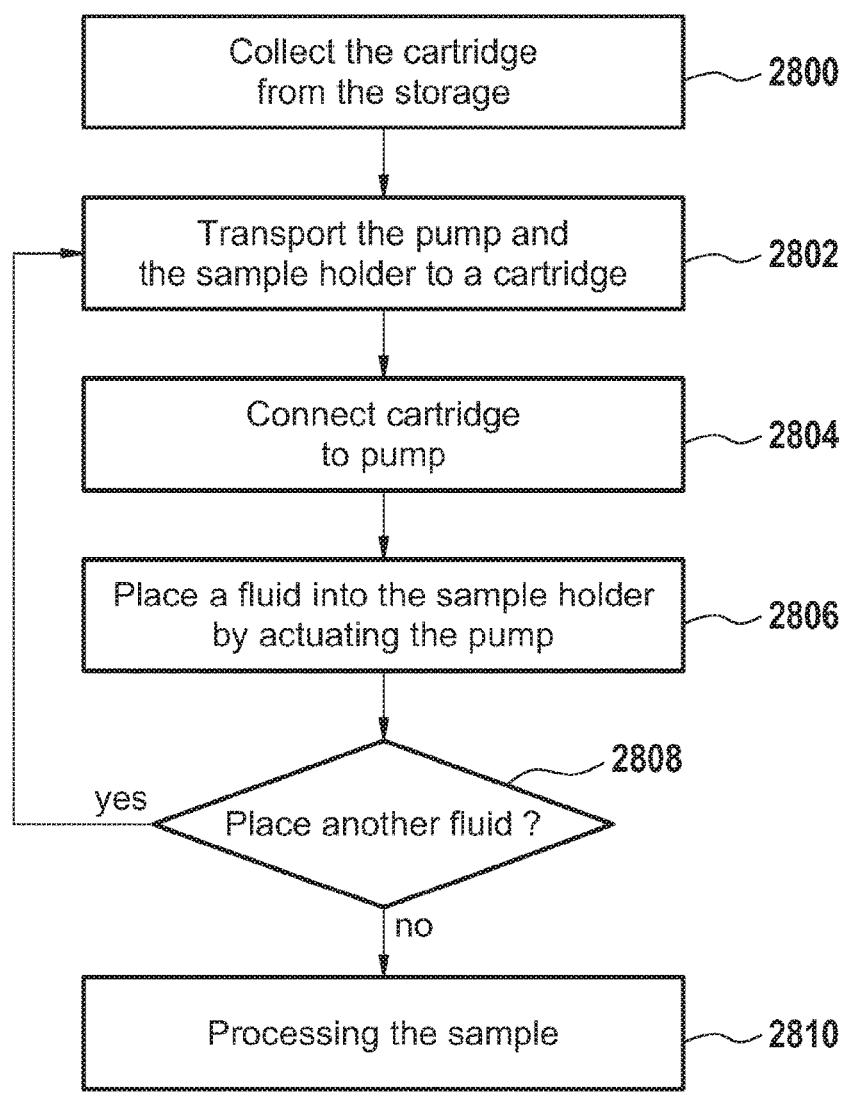

FIG. 28 shows a flowchart that illustrates a method of using the automatic analyzer 2700 of FIG. 27. First, in step 2800, cartridges are collected or removed from storage and installed into the automatic analyzer 2700. Next, in step 2802, the pump 2504 and the sample holder 2506 are transported to one of the cartridges 2502, 2502', 2502". Next, in step 2804, the translation mechanism 2508 connects the cartridge 2502, 2502', 2502" to the pump 2504. Next, in step 2806, the pump 2504 is actuated and a fluid is dispensed into the sample holder 2506. Step 2808 is a decision box. The decision is whether to place another fluid into the sample holder 2506. If the answer is yes the method returns to step 2802 and the pump 2504 is detached from the cartridge it is attached to and the pump 2504 and the sample holder 2506 are moved to a different cartridge. If the decision box 2808 is no then the processing of the sample 2507 proceeds to block 2810. In some instances the measurement unit 2510 may be used to perform the measurement of the analyte in the sample 2507.

Figure 29:
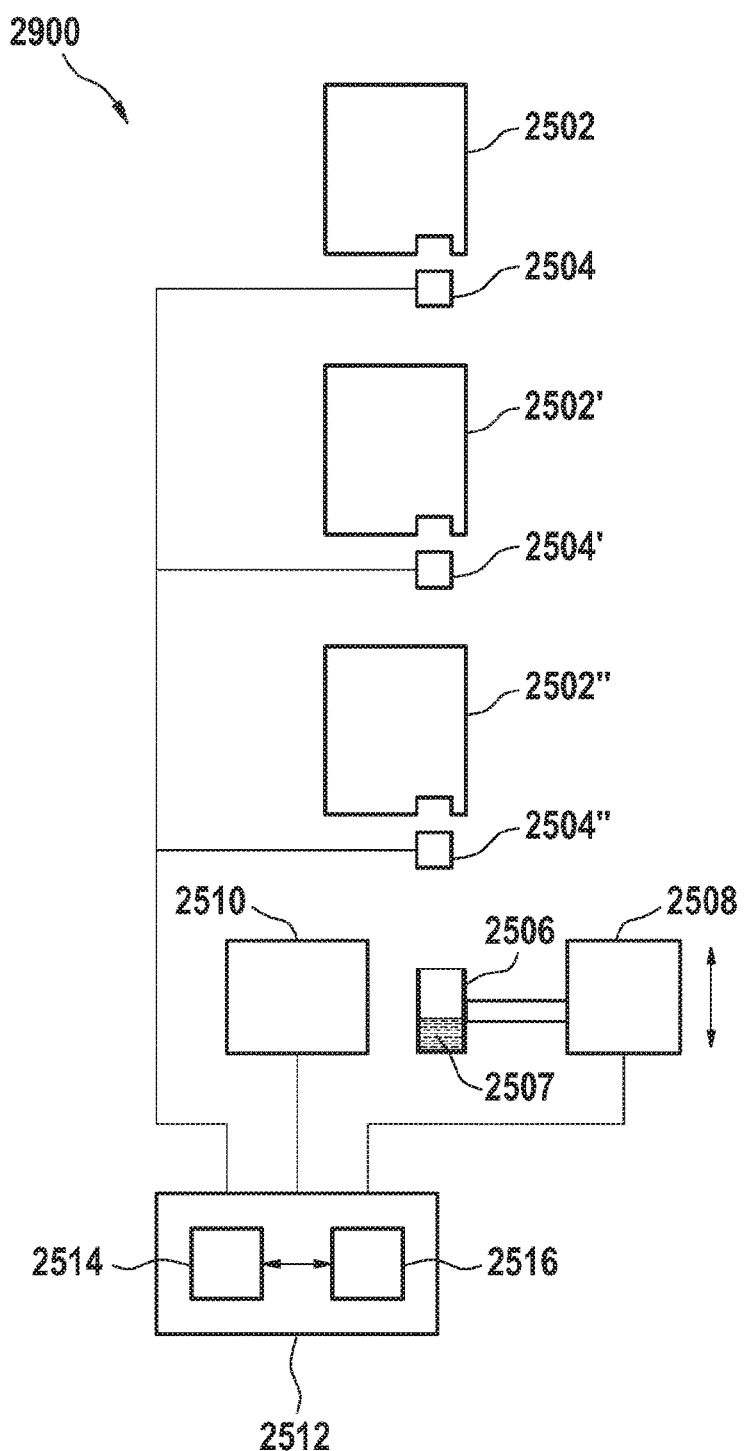

FIG. 29 shows a further example of an automatic analyzer 2900. The automatic analyzer 2900 is similar to the automatic analyzer 2500 shown in FIG. 25. The difference is that in FIG. 29 the pumps 2504, 2504', 2504" are a part of the automatic analyzer 2900 and not a part of the cartridges 2502, 2502', 2502".

In another example there may be a single pump or may be several pumps and the cartridges may be moved by the translation mechanism. For example, the pump and the sample holder may remain stationary and the translation mechanism moves the various cartridges to the pump where the fluid is then dispensed in order.

FIG. 30 shows a flowchart that illustrates a method of operating a variant of the automatic analyzer 2900 shown in FIG. 29. First, in step 3000, the cartridges 2502, 2502', 2502" are collected from storage and installed into the automatic analyzer 2900. Next, in step 3002, a cartridge is transported to one of the pumps 2504, 2504', 2504". There for instance may be a mechanism or apparatus that moves cartridges and installs them into a pump. Next, in step 3004, a cartridge 2502 is connected to the pump 2504, or the cartridge 2502' is connected to the pump 2504', or the cartridge 2502" is connected to the pump 2504". Next, in step 3006, the sample holder 2506 is transported to one of the pumps 2504, 2504', 2504" by the translation mechanism 2508. Next, in step 3008, the particular pump that the sample holder 2506 has been moved adjacent to is activated to place a fluid into the sample holder 2506. Block 3010 is a decision box that has the question to place another fluid into the sample holder 2506 or not. If the answer is yes then the translation mechanism 2508 moves the sample holder 2506 to a different pump 2504, 2504', 2504". If the answer is no then the method proceeds with the sample 2507 being processed in block 3012. The method may also contain the step of measuring the analyte in the sample using the measurement unit 2510.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modifications and variations come within the scope of the appended claims and their equivalents.

LIST OF REFERENCE NUMERALS 100 cartridge
102 rigid portion
104 flexible bladder
106 axis of symmetry of rigid portion
108 outlet
110 nozzle
112 line marking an opening
114 opening
116 inner cavity
118 inner cavity surface
120 bladder volume
122 fluid chamber filed with fluid
123 fluid
200 cartridge
300 cartridge
500 cartridge
500' cartridge 500 partially filled with fluid
500" cartridge 500 empty of fluid
502 cap
504 cap cavity
506 gas inlet
508 fluid inlet
510 seal
600 automatic analyzer
602 cartridge
602' cartridge
602" cartridge
604 actuator assembly
604' actuator assembly
604" actuator assembly
605 dispenser
606 sample holder
608 biological sample
610 relative movement means
612 relative movement
614 measurement system
620 computer
622 hardware interface
624 processor
626 user interface
628 computer storage
630 computer memory
632 analysis request
634 sensor data
636 analysis result
1100 empty cartridge
1100' cartridge 1100 filled
1200 empty cartridge
1200' cartridge 1200 filled
1300 empty cartridge
1300' cartridge 1300 filled
1400 empty cartridge
1400' cartridge 1400 filled
1600 cartridge
1602 detail region
1604 screw cap
1606 elastic seal
1606' elastic seal
1606" elastic seal
1700 top view
1702 side view
1800 top view
1802 side view
1900 empty cartridge
1900' cartridge with syringe attached
1900" filled cartridge
1902 luer lock with cap
1904 syringe
2000 cartridge
2002 screw cap
2100 cartridge
2102 diaphragm pump
2104 valve
2106 compressible chamber
2108 nozzle
2200 cartridge
2202 peristaltic pump
2204 tube
2300 cartridge
2302 piston pump
2400 view of piston pump
2402 view of piston pump
2404 view of piston pump
2406 view of piston pump
2408 rotatable portion
2410 piston
2412 pumping volume
2500 automatic analyzer
2502 cartridge
2502' cartridge
2502" cartridge
2504 pump
2504' pump
2504" pump
2506 sample holder
2507 sample
2508 translation mechanism
2510 measurement unit
2512 controller
2514 memory
2516 processor
2600 collect the cartridge from the storage
2602 transport the sample holder to a pump
2604 place a fluid into the sample holder by actuating the pump
2606 place another fluid?
2608 processing the sample
2700 automatic analyzer
2800 collect the cartridge from the storage
2802 transport the pump and the sample holder to a cartridge
2804 connect cartridge to pump
2806 place a fluid into the sample holder by actuating the pump
2808 place another fluid?
2810 processing the sample
2900 automatic analyzer
3000 collect the cartridge from the storage
3002 transport the cartridge to the pump
3004 connect cartridge to pump
3006 transport the sample holder to a pump
3008 place a fluid into the sample holder by actuating the pump
3010 place another fluid?
3012 processing the sample

What is claimed is:

1. A method of performing a measurement of an analyte in a sample using an automatic analyzer, wherein the automatic analyzer comprises:
   a cartridge for dispensing a fluid,
   a measurement unit for performing the measurement,
   a sample holder for receiving the sample, and
   a pump for pumping the fluid out of the cartridge and into the sample holder;
wherein the cartridge comprises:
   a rigid portion,
   a flexible bladder, and
   an outlet; wherein the outlet is attached to the rigid portion; wherein the rigid portion comprises an inner cavity; wherein the outlet is connected to the inner cavity;
   wherein the rigid portion comprises an opening; wherein the opening is connected to the inner cavity; wherein the flexible bladder seals the opening to form a fluid chamber from the inner cavity; wherein the fluid chamber is at least partially filled with the fluid; and
wherein the pump is connected to the outlet; and
wherein the method comprises:
   placing the sample into the sample holder;
   controlling the pumping of the fluid from the cartridge into the sample holder; and
   performing the measurement of the analyte using the measurement unit.

2. The method of claim 1, wherein the flexible bladder has an exterior surface, and wherein the exterior surface is exposed to constant pressure during pumping of the fluid from the cartridge into the sample holder.

3. An automatic analyzer for performing a measurement of an analyte in a sample, wherein the automatic analyzer comprises:
   a cartridge for dispensing a fluid,
   a measurement unit for performing the measurement,
   a sample holder for receiving the sample,
   a pump for pumping the fluid out of the cartridge to the sample holder,
   a memory for storing machine executable instructions, and
   a processor for controlling the automatic analyzer;
   wherein the cartridge comprises:
   a rigid portion,
   a flexible bladder, and
an outlet; wherein the outlet is attached to the rigid portion; wherein the rigid portion comprises an inner cavity; wherein the outlet is connected to the inner cavity; wherein the rigid portion comprises an opening; wherein the opening is connected to the inner cavity; wherein the flexible bladder seals the opening to form a fluid chamber from the inner cavity; wherein the fluid chamber is at least partially filled with the fluid; wherein the pump is connected to the outlet; and wherein execution of the instructions causes the processor to:
   control the pump to pump the fluid from the cartridge to the sample holder; and
   control the measurement unit to perform the measurement of the analyte.

4. The automatic analyzer of claim 3, wherein when the fluid chamber is filled with the fluid the flexible bladder is configured to expand out of the inner cavity to form a bladder volume; and wherein the bladder volume is defined by the opening and the flexible bladder.

5. The automatic analyzer of claim 4, wherein the flexible bladder is inelastic, and wherein when the fluid chamber is fully filled with the fluid the bladder volume is approximately equal to the volume of the inner cavity.

6. The automatic analyzer of claim 4, wherein the flexible bladder is elastic.

7. The automatic analyzer of claim 4, wherein the inner cavity has an inner cavity surface, and wherein when the fluid chamber is in an empty condition the flexible bladder is configured to cover the inner cavity surface.

8. The automatic analyzer of claim 4, wherein the cartridge further comprises a cap, wherein the cap forms a cap cavity, wherein the cap cavity is positioned about the opening, and wherein the cap cavity is configured to receive the flexible bladder when filled with the fluid.

9. The automatic analyzer of claim 8, wherein the cap is attached to the rigid portion to seal the cap cavity, and wherein the cap comprises a gas inlet that's configured for pressurizing and/or ventilating the cap cavity.

10. The automatic analyzer of claim 3, wherein the cartridge comprises a fluid inlet on the rigid portion, and wherein the fluid inlet is sealable with a seal.

11. The automatic analyzer of claim 3, wherein the outlet is circular, wherein the outlet has an outlet diameter, wherein the cavity is symmetric about an axis of symmetry, wherein the cavity has a cavity radius about the axis of symmetry, wherein the axis of symmetry passes through the opening and the outlet, and wherein the cavity radius is monotonically decreasing from the opening to the outlet.

12. The automatic analyzer of claim 3, wherein the cartridge further comprises a valve for sealing and unsealing the outlet and/or wherein the pump comprises a nozzle for dispensing the fluid.

13. The automatic analyzer of claim 3, wherein the cartridge is detachable from the pump.

14. The automatic analyzer of claim 3, wherein the pump has an inlet, and wherein the automatic analyzer further comprises a sealed coupling for attaching the pump inlet to the cartridge outlet.

15. The automatic analyzer of claim 3, wherein the measurement unit is any one of the following: a test strip analyzer, a urine test strip analyzer, a fluorescence spectrometer, a photospectrometer, a spectrometer, a scattered light spectrometer, a Chemiluminescence system, and electrochemiluminescense (ECL) measurement system, mass spectrometer, cell counter, optical imaging system, a staining system, a tissue diagnostics system, a turbidimetric measurement system, or a nephelometric measurement system.

16. The automatic analyzer of claim 3, wherein the automatic analyzer comprises a cartridge assembly, and wherein the cartridge assembly comprises the cartridge and the pump.

17. The automatic analyzer of claim 16, wherein the pump is permanently attached to the cartridge.

18. The automatic analyzer of claim 3, wherein the automatic analyzer further comprises multiple cartridges, wherein the automatic analyzer further comprises a translation mechanism for moving the pump between the multiple cartridges, wherein the translation mechanism is configured to attach the pump to any one of the multiple cartridges, and wherein the translation mechanism is configured to detach the pump from any one of the multiple cartridges.

19. The automatic analyzer of claim 3, wherein the automatic analyzer further comprises multiple cartridges, wherein the automatic analyzer comprises multiple pumps, wherein the automatic analyzer further comprises a translation mechanism for either moving the sample holder to each of the multiple cartridges or for moving each of the multiple cartridges to the sample holder.

20. A cartridge assembly, wherein the cartridge assembly comprises:
   a cartridge for dispensing a fluid through an outlet, and
   a pump for pumping the fluid in the cartridge through the outlet;
wherein the cartridge comprises:
   a rigid portion, and
   a flexible bladder;
wherein the outlet is attached to the rigid portion; wherein the rigid portion comprises an inner cavity; wherein the outlet is connected to the inner cavity; wherein the rigid portion comprises an opening; wherein the opening is connected to the inner cavity; wherein the flexible bladder seals the opening to form a fluid chamber from the inner cavity; wherein the pump is connected to the outlet; wherein when the fluid chamber is filled with the fluid the flexible bladder is configured to expand out of the inner cavity to form a bladder volume; and wherein the bladder volume is defined by the opening and the flexible bladder.

* * * * *